US011820744B2

(12) United States Patent
Mir

(10) Patent No.: US 11,820,744 B2
(45) Date of Patent: Nov. 21, 2023

(54) GENERATORS FOR 1-METHYLCYCLOPROPENE RELEASE FROM CARRIER COMPLEX

(71) Applicant: Nazir Mir, Somerset, NJ (US)

(72) Inventor: Nazir Mir, Somerset, NJ (US)

(*) Notice: Subject to any disclaimer, the term of this patent is extended or adjusted under 35 U.S.C. 154(b) by 0 days.

(21) Appl. No.: 17/693,354

(22) Filed: Mar. 12, 2022

(65) Prior Publication Data

US 2022/0306554 A1  Sep. 29, 2022

Related U.S. Application Data

(63) Continuation of application No. 17/246,663, filed on May 2, 2021, now Pat. No. 11,306,046, which is a continuation-in-part of application No. 16/686,123, filed on Nov. 16, 2019, now Pat. No. 11,033,870.

(51) Int. Cl.
| | |
|---|---|
| *C07C 7/10* | (2006.01) |
| *B01J 7/02* | (2006.01) |
| *C07C 7/152* | (2006.01) |
| *A23B 7/144* | (2006.01) |
| *B01F 27/05* | (2022.01) |
| *B01F 35/30* | (2022.01) |
| *C07C 13/04* | (2006.01) |
| *B01F 35/71* | (2022.01) |

(52) U.S. Cl.
CPC .............. *C07C 7/10* (2013.01); *A23B 7/144* (2013.01); *B01F 27/05* (2022.01); *B01F 35/30* (2022.01); *B01J 7/02* (2013.01); *C07C 7/152* (2013.01); *B01F 35/7176* (2022.01); *C07C 13/04* (2013.01)

(58) Field of Classification Search
CPC . C07C 7/10; C07C 7/152; C07C 13/04; B01J 7/02; B01F 15/00435; B01F 7/00008; B01F 15/0243; A23B 7/144
See application file for complete search history.

(56) References Cited

U.S. PATENT DOCUMENTS

| 6,897,185 B1 * | 5/2005 | Chang | A01N 27/00 |
| | | | 504/357 |
| 2014/0080710 A1 * | 3/2014 | Zhang | A01N 25/10 |
| | | | 504/357 |

* cited by examiner

*Primary Examiner* — Christopher P Jones
*Assistant Examiner* — Phillip Y Shao
(74) *Attorney, Agent, or Firm* — RUEPPELL LAW

(57) ABSTRACT

Providing a method for generating and releasing 1-MCP gas from a complex carrier through the use of a 1-MCP generator that enables the application of at least one physical, releasing force to a carrier complex and/or mixture comprising water and the carrier complex, or the interaction of steam with a carrier complex and/or mixture comprising water and the carrier complex, over a determined period of time.

20 Claims, 26 Drawing Sheets

```
                    ┌─────────────┐
                    │   START     │
                    └──────┬──────┘
                           │
                           ▼
        ┌──────────────────────────────────────┐
        │  establishing a mixture, the mixture │
        │  comprising a carrier complex in water, in a │─── 510
        │  mixing tank, the carrier complex    │
        │  comprising 1-MCP and a carrier      │
        └──────────────────┬───────────────────┘
                           │
                           ▼
        ┌──────────────────────────────────────┐
        │ releasing a gaseous form of 1-MCP from the carrier │
        │ complex by the application of a releasing force    │
        │ provided through operational connection of the     │─── 520
        │ mixing tank to a motor, wherein the applied        │
        │ releasing force promotes a desirable foam by-      │
        │ product profile and compliant impurity profile for │
        │ the released 1-MCP gas                             │
        └──────────────────┬───────────────────┘
                           │
                           ▼
                    ┌─────────────┐
                    │    END      │
                    └─────────────┘
```

Fig. 5

```
                    ┌─────────┐
                    │  START  │
                    └────┬────┘
                         │
                         ▼
    ┌──────────────────────────────────────────┐
    │   establishing a mixture, the mixture    │
    │  comprising a carrier complex in water,  │──[ 910 ]
    │        in a mixing tank, the carrier     │
    │    complex comprising 1-MCP and a carrier│
    └──────────────────┬───────────────────────┘
                       │
                       ▼
    ┌──────────────────────────────────────────┐
    │ releasing a gaseous form of 1-MCP from   │
    │   the carrier complex by the application │
    │   of a releasing force provided through  │
    │  operational connection of the           │──[ 920 ]
    │  mixing tank to an electromagnetic coil, │
    │  wherein the applied releasing force     │
    │  promotes a desirable foam by-product    │
    │  profile and compliant impurity profile  │
    │       for the released 1-MCP gas         │
    └──────────────────┬───────────────────────┘
                       │
                       ▼
                  ┌─────────┐
                  │   END   │
                  └─────────┘
```

Fig. 9

GENERATORS FOR 1-METHYLCYCLOPROPENE RELEASE FROM CARRIER COMPLEX

CROSS-REFERENCE TO RELATED APPLICATION(S)

This application claims the benefit and priority of U.S. patent application Ser. No. 16/686,123, filed Nov. 16, 2019, now U.S. patent Ser. No. 11/033,870, and U.S. patent application Ser. No. 17/246,663, filed on May 2, 2021, both are herein incorporated by reference in their entireties.

BACKGROUND

Cyclopropene compounds have various applications and uses in the chemical industry, in particular, 1-methylcyclopropene (1-MCP), and its related analogs, are understood as highly effective in controlling and/or inhibiting the adverse effects of ethylene in plants thereby promoting delayed ripening and senescence (see Blankenship & Dole, 2003) (see also U.S. Pat. No. 5,518,988). As such, commercially (cost), efficient and effective generation, storage and use of these compounds, such as 1-MCP, have become significantly important considerations in the industry.

Further, additional costs and significant safety concerns are raised due to 1-MCP and its analogs being relatively unstable. This instability is due to their reactive nature, particularly the potential for undergoing reactions, such as "ene" and/or oxidation. Due to the inherent volatility and reactivity of cyclopropene compounds, they cannot be stored in the gaseous state for an extended period of time. Additionally, cyclopropene compounds, such as 1-MCP, is a gas under room temperature and is flammable, and thus poses a risk of explosion when compressed. Therefore, 1-MCP is often synthesized and then trapped into selective solid matrices or carrier materials for storage, handling, and application. The instability and the safety concerns for the 1-MCP gas can be addressed in various ways and have been addressed through various means, such as the encapsulating techniques of 1-MCP into α-cyclodextrin as disclosed in U.S. Pat. No. 6,017,849. During application, the 1-MCP/α-cyclodextrin is usually dispersed in water which can displace 1-MCP in α-cyclodextrin to release 1-MCP. One issue with 1-MCP release using water is that α-cyclodextrin powder clumps, making it difficult to be dispersed, and the height of the water column would also create pressure to hinder the release of 1-MCP. To facilitate the 1-MCP release, several approaches for commercial application have been disclosed.

One approach is using air pump to introduce air in water to create movement in water and facilitate contact between water and α-cyclodextrin/1-MCP powder to achieve complete release of 1-MCP as disclosed in U.S. Pat. Application No. 20030220201. But foam can be formed because α-cyclodextrin has both hydrophobic and hydrophilic groups that can trap air. Foaming may cause overflow of water containing α-cyclodextrin/1-MCP from the generator, which may result in residual chemicals on the ground, which leads to worker safety risks and difficulty in cleaning.

Several approaches using chemical additives were also disclosed to improve mixing and dispersing. U.S. Pat. No. 6,444,619 disclosed compositions of agglomerated α-cyclodextrin/1-MCP powder with other ingredients, including binder, lubricant, release agent, dispersant, wetting agent, spreading agent, dispersing agent, stickers, adhesives, defoamer, thickener and emulsifying agent, to form a tablet, and thus help handling, and slow down the initial release to limit worker exposure to 1-MCP. U.S. Pat. No. 6,426,319 disclosed compositions using superabsorbent polymer and deliquescent compounds to facilitate the contact between water and α-cyclodextrin/1-MCP powder to achieve complete release of 1-MCP. U.S. Pat. No. 6,762,153 disclosed compositions of α-cyclodextrin/1-MCP effervescent tablet which generates $CO_2$ bubbling to facilitate the contact between water and α-cyclodextrin/1-MCP to achieve complete release of 1-MCP. U.S. Pat. No. 8,541,344 disclosed compositions using chelating agents which reduces the effect of metal ions on 1-MCP, as some metal ions can react with 1-MCP, to achieve complete release.

The focus of the abovementioned inventions is on achieving complete release of 1-MCP; however, the additives used in these inventions may lead to other reactions with 1-MCP to generate undesirable impurities, which are volatile or gaseous compounds that are formed from the reactants and the reaction. Controlling the impurity levels of the end product is a regulatory compliance matter enforced by the United States of America Environmental Protection Agency (US EPA). Impurity levels are strictly regulated by the US EPA, which requires 1-MCP impurity profiles to be below 0.1% of the total 1-MCP loading and the levels of chlorinated compounds 1-chloro-2-methylpropene (1-CMP) and 3-chloro-2-methylpropene (3-CMP) below 0.05% of total 1-MCP loading. Thus, significant commercial advantage and regulatory compliance can be realized through careful control over the release and impurity profile for any 1-MCP generation system being employed.

Another challenge in releasing 1-MCP is the low temperature in the target produce treatment rooms. Once the produce such as apples and pears are harvested, they are cooled to remove field heat, after which they are stored under refrigeration (−0.5° C. to 5° C.) or controlled atmospheric condition which in addition to refrigeration has well defined cultivar specific $O_2$ and $CO_2$ atmosphere to maintain quality during storage. The low temperature is effective to slow down the physiological degradation of the produce and extend shelf life, but can also affect the dissolution of 1-MCP complex in water; for example, the solubility of α-cyclodextrin, a commonly used 1-MCP encapsulant, decreases as temperature decreases (Jozwiakowski and Connors, 1985). Also, the encapsulation process is usually an exothermic process and in turn the dissociation and subsequent release of 1-MCP is favored by increasing temperature. Unfortunately, there is no commercial 1-MCP generator considering the effect of temperature on the release of 1-MCP. Addressing the factor of temperature can provide multiple practical advantages such increased solubility of 1-MCP complex and increasing the dissolution rate of the complex and release rate of 1-MCP and thus providing the required 1-MCP at an early stage to the fruits.

In addition to α-cyclodextrin, 1-MCP carried by other solid matrices such as metal organic framework and activated carbon are also commercially available, but there is no generator that can effectively release 1-MCP from these matrices reported.

The aim of the present invention is to use only water to completely release 1-MCP from cyclodextrins or their derivatives and formulations, and other solid matrices, with no or minimal foaming or generating any undesirable impurities.

BRIEF DESCRIPTION OF THE DRAWINGS

The objects and advantages of the invention will be understood by reading the following detailed description in conjunction with the drawings in which:

FIG. 5 is a block diagram illustrating a first preferred method for releasing a 1-MCP gas in accordance with an exemplary embodiment of the current invention;

FIG. 9 is a block diagram illustrating a fifth preferred method for releasing a 1-MCP gas in accordance with an exemplary embodiment of the current invention;

DETAILED DESCRIPTION

Figure 1:
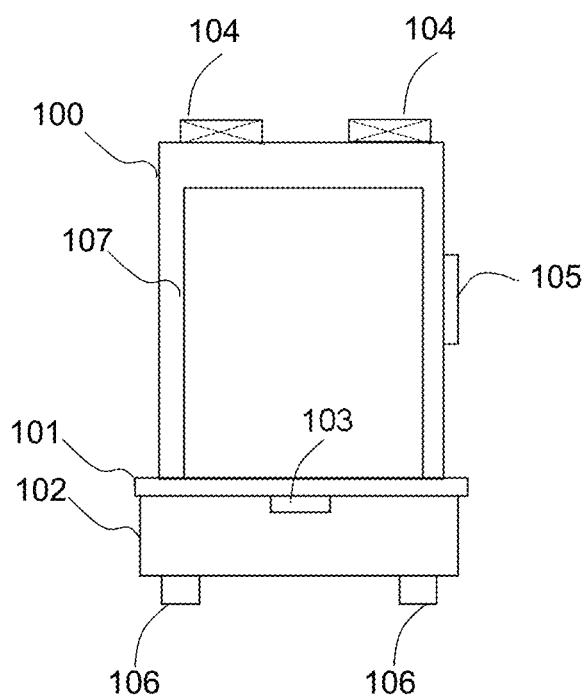
FIG. 1 is an illustration of a two dimensional rotational motion 1-MCP generator in accordance with the current invention.

Preferred, exemplary and contemplated embodiments of the current invention comprise methods, systems and apparatus used for achieving the release of a 1-MCP gas. It is contemplated for at least some to all embodiments of the current invention that prior to the release of the 1-MCP in gas form, the 1-MCP is at least temporarily complexed, contained or stored in a carrier complex, thereby having an initial 1-MCP state. This initial 1-MCP state can provide the 1-MCP in various forms, such as in a solid matrix form and the like as may be contemplated. As such, the 1-MCP/complex may also be referred to herein as the "carrier complex", "complexed carrier", "complexed 1-MCP", "1-MCP complex", "1-MCP/complex carrier" or "complex". When a complex is included in a mixture with water or distilled water (ionized or de-ionized) the resulting mix can be referred to as the "mixture", "reaction mixture", "clean mixture", "complex(ed) mixture", "release mixture" and the like as may be identified herein below or contemplated by those skilled in the art. In exemplary embodiments, a mixture can have an amount of carrier complex that can range from 0.001 kg to 10 kg, preferably 0.01 kg to 6 kg and more preferably 0.02 kg to 1 kg. Further, the ratio of carrier complex to water in exemplary mixtures can range from 1:500 to 1:5 and more preferably 1:100 to 1:10. Thus, for embodiments of the current invention, prior to the release of the 1-MCP in gas form, the 1-MCP can be at least temporarily contained or stored in a carrier complex, thereby having an initial 1-MCP state, and can be established separately or included in a water-based mixture.

Achieving the release of 1-MCP gas from a complex in embodiments of the current invention is, at least in part, promoted and/or significantly accomplished by the direct or indirect application of a physical (releasing) force to the complex. As such the releasing force applied to complexed 1-MCP can result in the dissociation of 1-MCP from the carrier it had been complexed with. The dissociation of 1-MCP can result in the release of 1-MCP in gas form from the carrier complex. The releasing force can be directly or indirectly applied to a separate, initial 1-MCP state and/or to a mixture comprising water mixed with a preliminary solid matrix, such as a 1-MCP/complex carrier. In any of the exemplary and contemplated embodiments, the releasing force(s) (i.e., physical and steam) that can be generated and applied for promoting and/or significantly accomplishing the release of a 1-MCP gas from an initial 1-MCP state can be provided by a generator device, also referred to herein as a "generator", "1-MCP generator", or "motor". The generator can be configured and include various and numerous operationally connected component features, such as a motor, rotational mechanism, stirring mechanism, vibrational mechanism, control panel/system, housing(s), separator(s), platform(s), ventilation mechanism(s), blower mechanism(s) and the like as may be contemplated. The generator may be powered via any means contemplated and as may be appropriate for the environment within which the generator is or to be utilized. Additional mechanisms and/or devices, such as jars, containers, storage devices, and the like, which can be made of any materials (i.e., plastic, glass, and the like), can be employed with embodiments of the current invention. Herein below are described and presented several examples that provide additional description for and features of a generator(s) and various methods and processes employed and contemplated for exemplary embodiments of the current invention.

The force(s) that may be generated and applied by a 1-MCP generator of the current invention can comprise, without limitation, a rotational, stirring, mixing, vibrational and/or other releasing force(s), as may be contemplated by those skilled in the art. The generation of the physical force can be accomplished through the use of any device, mechanism and the like that can accomplish the desired force generation capability as may be contemplated by those skilled in the art. The generated releasing (physical) force can be directly or indirectly applied, via the use of various and contemplated mechanisms, devices and the like, which may be an integral or connectable and/or removable part of a generator employed for embodiments of the current invention. The releasing force can be applied to the initial 1-MCP state and/or to a water-based mixture within which the complexed 1-MCP may be found for embodiments of the current invention. By way of example, and without limitation, a direct application of a releasing force can be accomplished by means of a generator employing a rotating stirring rod that stirs a water-based mixture including the complexed 1-MCP. Alternatively, an indirect application of a releasing force can be accomplished by means of a generator employing a vibrating mechanism that provides and applies a "shaking" or "oscillation" to a container within which a water-based mixture including the complexed 1-MCP can be stored.

Another releasing force that can be applied to a 1-MCP complex, in exemplary and contemplated embodiments of the current invention, can be in the form of water vapor (steam). For example, water can be heated until it reaches a sufficient temperature to transition into a vapor phase, otherwise known as steam. The steam can be allowed to interact with a complexed 1-MCP within a generator. Such generator may also be understood and referred to herein as a "steam generator" and the like as contemplated and described further herein. The interaction of the steam with the complexed 1-MCP can result in the dissociation of 1-MCP from the carrier it had been complexed with. The dissociation of 1-MCP results in the release of 1-MCP in gas form from the carrier complex. It is understood that the application of the steam or other physical releasing force(s) can and may occur in isolation from, sequentially and/or concurrently with one another. Therefore, the generators of the current invention may be understood as capable of being configured and providing one or more of the releasing forces described herein for the current invention.

Release of 1-MCP gas, as may be provided, contemplated and described for any of the exemplary embodiments of the current invention, can further advantageously promote a more complete release of a 1-MCP gas from a carrier complex than has previously been able to be accomplished in the prior art. The promotional capabilities can mean that greater than ninety-six percent (>96%), more preferably, approaching (close to) and/or significantly one hundred (100%) percent, of the 1-MCP gas can be and/or is released from the 1-MCP/carrier complex. The promotional release capabilities can be realized for a separate 1-MCP complex or when in mixture with water. The release of 1-MCP gas from a carrier complex and/or a mixture comprising the carrier complex in water into the headspace of the 1-MCP generator or its surrounding environment is known and described herein as a '1-MCP Release Process' for the current invention.

For exemplary embodiments of the current invention, it is understood that a 1-MCP generator is a device having numerous and various capabilities, including being enabled to generate and capable of applying one or more releasing force(s), directly or indirectly, to a mixture and/or 1-MCP/carrier complex. Further, the releasing force capabilities can include, without limitation, the capability of exposing the mixture and/or 1-MCP complex to interaction with water vapor (steam). Other characteristics and capabilities, including various releasing force enablement and capabilities, as are and may be contemplated by those skilled in this field for the current invention without departing from its current scope.

The embodiments of the current invention can provide for the release of 1-MCP gas having an impurity profile that meets or exceeds regulatory compliance standards. As such, and described herein below, the current invention can promote and significantly achieve the release of 1-MCP gas with an impurity profile below 0.1% of the total 1-MCP and with levels of chlorinated compounds 1-chloro-2-methylpropene (1-CMP) and 3-chloro-2-methylpropene (3-CMP) below 0.05% of total 1-MCP loading.

The embodiments of the current invention can further provide an advantageous and desirable foam by-product profile during and throughout the process(es) of releasing 1-MCP gas from complex. It is contemplated that the current invention promotes a significant reduction in or avoidance of the generation of a foam by-product during the release of 1-MCP in gas form. It can be contemplated that if a foam by-product were to be generated during and throughout the process(es) of releasing 1-MCP gas it may be found within a container, reaction vessel or mixing tank, or an interior space therein, of embodiments of the current invention.

A foam by-product profile can be understood in reference to the presence or absence of a measurable amount of a foam by-product as may or may not be generated during the release of 1-MCP gas in accordance with embodiments of the current invention. The presence and amount of a foam by-product can be identified and referred to herein as a "foam height". A foam height, or lack thereof, can be understood as establishing the foam by-product profile. The current invention promotes a reduced or significantly avoids any foam by-product profile during the release of 1-MCP gas, wherein if any foam by-product (foam height) is found it can range from less than or equal to 3.1 cm, 2.5 cm to 2.0 cm, preferably less than or equal to 2.0 cm or, more preferably, 1.0 cm to 0 cm. As described herein, the current invention promotes a foam height that is non-existent or at least one that is generally, significantly less than that found in comparison to other methods, systems and apparatus that have been, may be and are employed in the prior art for the release of 1-MCP gas. It is therefore understood that this capability of the current invention provides a critical advantage in comparison to the prior art by promoting a significant reduction in or avoidance of the generation of a foam by-product during the release of 1-MCP gas and therefore the avoidance of any harmful effects, such as spillage outside the generator, that may be caused by the presence of any foam by-product in amounts greater than that described herein for the current invention. This promotional capability is also referred to herein as the "by-product avoidance capability(ies)" and/or "foam avoidance capability(ies)".

A contemplated preferred method embodiment for the current invention for releasing a 1-MCP gas can comprise establishing a mixture, also referred to herein as a "release mixture" or "releasing mixture", in an interior space of a mixing tank (also referred to herein as a mixing vessel, reaction vessel, releasing tank and the like), wherein the release mixture comprises a carrier complex, of 1-MCP complexed with at least one carrier, in water. The release of a gaseous form of 1-MCP from the carrier complex can be accomplished, at least in part, by the application of a releasing (physical) force provided through operational connection of the mixing tank to a motor, wherein the applied releasing force promotes a movement of the mixing tank and/or the release mixture therein, dissociation of 1-MCP from the carrier in the release mixture and, thereby, release of 1-MCP in gas form. The process of releasing the 1-MCP gas, as contemplated and provided by the embodiments herein, can further promote and/or provide a desirable foam by-product profile and a compliant impurity profile for the released 1-MCP gas.

Another contemplated preferred method embodiment for the current invention for releasing a 1-MCP gas can comprise establishing a carrier complex, the carrier complex comprising 1-MCP complexed with at least one carrier, on a separator within an interior space of a vessel or housing, the vessel or housing can further comprise a water reservoir for at least temporarily storing water, and wherein the separator prevents direct contact between the carrier complex and water. The water can be heated until it converts, at least some of the water, into vapor phase (steam). The release of a gaseous form of 1-MCP from the carrier complex is promoted and accomplished through the interaction of the steam with the carrier complex. The steam interaction promotes dissociation of 1-MCP from the carrier in the carrier complex and release of 1-MCP in gas form. The process of releasing the 1-MCP gas can further promote and/or provide a desirable foam by-product profile and a compliant impurity profile for the released 1-MCP gas in accordance with the current invention.

It is further contemplated for preferred embodiments of the current invention that a system for performing the methods of releasing 1-MCP gas is provided. The system comprising a 1-MCP generator including a motor operationally connected to a storage device/mixing tank. Contained within an interior space of the storage device is a release mixture comprising a 1-MCP carrier complex in water. The motor, via operational connection, is capable of applying a physical (releasing) force to the storage device and, thereby, promotes a movement of the storage device.

The movement imparted to the storage device can further promote the dissociation of 1-MCP from the carrier in the release mixture and release of 1-MCP in gas form. The releasing of the 1-MCP gas provided by the system embodiment(s) can further promote and/or provide a desirable foam by-product profile and a compliant impurity profile for the released 1-MCP gas in accordance with the current invention.

In other contemplated preferred embodiments of the current invention a system for performing the methods of releasing 1-MCP gas is provided. The system comprising a 1-MCP generator including a generator housing removably connected to a base. The base comprises a base receptacle or reservoir within which a heating element, such as a heating plate, heating coil and the like, is contained and protected by a cover. The base receptacle further comprises a water reservoir for holding water. The base receptacle provides an operational connection between the heating element and water contained in the water reservoir, allowing the heating of the water by the heating element. A separator device (also referred to herein as a "separator", "perforated mesh stand", "separator mixing tank" and the like as may be contemplated) can be positioned and/or included within the generator housing. It can be understood that the separator device is separate from, integral with and/or connectable to the generator housing and/or base. The separator device can carry, store, handle, process and the like a carrier complex comprising 1-MCP complexed with a carrier. The separator device prevents direct contact between the carrier complex and water contained in the water reservoir. The heating element, via operational connection within the base, is capable of applying heat to the water in the water reservoir and heating the water to vapor phase, thereby generating steam. Within the generator housing the steam interacts with the carrier complex positioned on the separator device, wherein the steam interaction promotes dissociation of 1-MCP from the carrier in the carrier complex and release of 1-MCP in gas form. The released 1-MCP gas provided by the system embodiment(s) can further promote and/or provide a desirable foam by-product profile and a compliant impurity profile for the released 1-MCP gas in accordance with the current invention. It shall be understood that for any generator embodiment contemplated by the current invention the configuration, features and/or characteristics may vary and/or be changed and established in any manner as may be contemplated by those skilled in the art and does not depart from the scope contemplated for the current invention.

In other contemplated preferred embodiments of the current invention a system for performing the methods of releasing 1-MCP gas is provided. The system comprising a 1-MCP generator including a generator housing removably connected to a base. The base includes a base receptacle or reservoir within which a heating element, such as a heating plate, heating coil and the like, is contained and protected by a cover. The receptacle also includes a water reservoir for holding water. The water reservoir provides an operational connection between the heating element and water contained therein, allowing the heating of the water by the heating element. Within the generator housing and enabled to be removably connected with the receptacle, but separate from the generator housing and water reservoir, is a separator mixing tank. Water can be contained within the water reservoir and the separator mixing tank can carry, store, handle, process and the like a carrier complex comprising 1-MCP complexed with a carrier. The separator mixing tank prevents direct contact between the carrier complex and water. The motor, via the operational connection to the separator mixing tank, is capable of applying a physical force to the separator mixing tank and/or the contents therein. The heater, via the operational connection to the water reservoir, is capable of applying heat to the water in the water reservoir. Thus, the heater heats the water to vapor phase, thereby generating steam, and the steam interacts with the carrier complex within the separator mixing tank. In the current embodiment, the motor, via the operational connection, is capable of applying a physical force to the storage device and, thereby, promoting a movement of the storage device. Dissociation of 1-MCP from the carrier in the carrier complex is promoted by the movement provided to the carrier complex by the physical force applied and interaction with the steam. The dissociation of the 1-MCP results in the promotion of the release of the 1-MCP in gas form. The releasing of the 1-MCP gas provided by the system embodiment(s) can further promote and/or provide a desirable foam by-product profile and a compliant impurity profile for the released 1-MCP gas in accordance with the current invention.

In contemplated preferred embodiments of the current invention a 1-MCP generator mechanism, for performing the method(s) and utilization in the system(s) of the embodiments of the current invention, is provided. The 1-MCP generator can comprise a force generation mechanism, such as a motor that may be variously configured and enabled to provide power, for generating a physical (releasing) force ("release force" or "releasing force" as previously described). The force generation mechanism can be operationally connected directly with other component features of a 1-MCP generator and/or indirectly with other component features, such as through operational connection with various force application mechanisms and/or device(s). For example, a force application mechanism may be provided as an integrated receptacle mechanism that is operationally connected to the force generation mechanism directly. The integrated receptacle mechanism may be variously sized and configured and provide a container or vessel (that can be understood and as previously indicated may be referred to herein as a "storage device", "mixing tank", "reaction vessel", "rotating element" and the like as may be contemplated) that enables the storage, processing and/or handling of materials, such as the carrier complex either alone or mixed in water in a mixture. The direct operational connection in such a contemplated embodiment of the 1-MCP generator can apply a physical force (directly or indirectly) to the materials within the integrated receptacle, thereby promoting the release of 1-MCP gas. By way of example, a 1-MCP generator can provide a force generation mechanism in operational connection with a force application mechanism, whereby a rotational force is generated and applied. With such a direct operational connection, as that described above, it is contemplated that a rotational (mixing) force can be provided through the movement of the mixing tank (rotating element) around a fixed axis. Various exemplary embodiments of the current invention can be provided wherein a rotating element moves around a fixed axis (or point) of rotation, such as described herein, and the like as may be contemplated by those skilled in the art.

In other exemplary embodiments of the current invention, a receptacle mechanism can be configured to enable the 1-MCP generator with the capability to provide for the removable connection with a secondary device. For example, the receptacle mechanism can be a holding platform or such other mechanism that enable a removable connection with a secondary device, such as a mixing tank, container, vessel and the like. Such a receptacle may be variously sized and configured to enable removable interaction with variously sized and configured secondary devices and as may be contemplated by those skilled in the art. It is contemplated in such embodiments that within the secondary device the storage, processing and/or handling of materials, such as the carrier complex either alone or in mixture (with water), is provided. With such an indirect operational connection, as that described above, it is contemplated that the rotational (mixing) force can be provided through various means, such as the movement of the receptacle mechanism which is then translated to the secondary device or the movement of the secondary device in relation to the receptacle mechanism, whereby the movement provided is contemplated to be around a fixed axis. In such exemplary embodiments the secondary device can be understood and referred to as a storage device, mixing tank, rotating element and the like. Numerous contemplated exemplary embodiments of the current invention can be provided wherein variously sized and configured secondary devices (which may also be referred to herein as a "rotating element") are enabled by operational connection with a 1-MCP generator to move around a fixed axis (or point) of rotation, such as described herein, and as may be contemplated by those skilled in the art.

In other exemplary embodiments it is contemplated that the force generation and application mechanism is a stirring mechanism that, in operational concert with a storage device (a.k.a., mixing tank, reaction vessel and the like), and in operational connection with a motor of a 1-MCP generator is capable of applying a physical (stirring) force to various objects and/or material(s)) that can be contained within the storage device. Stirring refers to moving an object and/or materials around in order to mix it thoroughly. As such, it is contemplated for exemplary embodiments of the current invention that the object and/or materials that will have a stirring force applied are at least partially included in a liquid, e.g., water or distilled water (ionized or de-ionized) or other substance that allows or enables the mixing. As described, such a mixture may be referred to herein as a "release mixture", can be stored or contained in the storage device. For exemplary embodiments of the current invention, a stirring (release) force can be provided or applied by the operational connection of a mixing mechanism with the mixture (release mixture). It is contemplated for exemplary embodiments of the current invention that the mixing mechanism can be variously configured as and comprise alternative or one or more mixing elements, such as a stir bar (magnetic or otherwise), a mixing rod, and the like as may be contemplated by those skilled in the art in operational connection with and/or operationally engaged by a force generator mechanism, such as a motor or electromagnetic element. In contemplated and exemplary embodiments, a mixing element may be configured as a magnetic stir bar and the like that can be imparted with a movement, via operational connection to an electromagnetic element (device or mechanism), such as an electromagnetic coil or other mechanism and/or device as may be contemplated by those skilled in the art, and thereby enabled to apply a stirring (rotational) force to a complex and/or mixture. For specific exemplary embodiments described herein, the stir bar can be a magnetic stir bar and is positioned within a storage device. It is contemplated that various mixing elements can be established in operational connection with one or more of the force generation mechanisms, such as the motor and/or electromagnetic coil. The operational connection(s) established can be accomplished in various manners as may be contemplated by those skilled in the art. In such embodiments, the mixture (release mixture) when present in and/or added to the storage device/mixing tank may, therefore, the mixing element (i.e., stir bar) can interact with or be in operational contact with the mixture and, as such, the mixture can have a mixing (rotational) force applied to it. In additional contemplated exemplary embodiments, a mixing rod can be variously configured and as such may comprise a shaft element that either by itself or by connection with one or more blades, propellers and the like can be placed in operational contact with and apply a stirring (rotational) force to a mixture that is contained within a storage device (mixing tank).

The stirring force that may be applied refers to the rotational movement of the mixing mechanism, element(s) and/or rod with or without one or more blades, propellers and the like, and through interaction and/or operational contact with a mixture (release mixture) and thereby can promote and provide for the mixing (rotation) of the mixture. The stirring (mixing) force that can be provided by the current invention promotes mixing and the release of 1-MCP gas from the mixture and avoidance of an undesirable foam by-product profile. Promoting the avoidance of foam generation, also promotes the avoidance of foam generation-induced mixture overflowing a mixing tank, reaction vessel and the like, which could potentially result in various adverse events, such as the spilling on the ground of at least some mixture and/or foam by-product or non-compliant impurity profiles.

In exemplary embodiments of the current invention, it is contemplated that the force generation and application mechanism is a vibration force mechanism that in operational concert with a storage device (a.k.a., mixing tank) is capable of applying a physical (vibrational or oscillatory) force to the storage device and/or various objects and/or material(s)) that can be contained within the storage device. Vibration refers to a mechanical phenomenon whereby oscillations occur about an equilibrium point. For exemplary embodiments of the current invention the application of a vibration force can be understood as generating an oscillation (oscillatory movement) in the storage device (mixing tank) and/or various objects and/or materials, such as a mixture (release mixture), contained within or inside the storage device. The vibration force that can be provided by the current invention promotes mixing and the release of 1-MCP gas from the mixture and avoidance of foam generation, foam generation-induced mixture overflowing a mixing tank, reaction vessel and the like, which could potentially result in various adverse events, such as the spilling on the ground of at least some mixture and/or foam by-product or non-compliant impurity profiles.

In the contemplated and preferred embodiments, the use of a mechanism, referred to herein as a "generator", "1-MCP generator", "generator system" and/or "releasing mechanism", provides for the application of a physical force to a device for accomplishing various movements of the device and materials contained therein, such as a rotational, stirring, vibrational and/or other force(s) as may be contemplated by those skilled in the art. The 1-MCP generator can comprise various connectable and/or re-connectable component features and devices, such as a motor and an electromagnetic element (device or mechanism), such as an electromagnetic coil operationally connected to a device, wherein the device can be a storage device, mixing tank and the like as described herein and contemplated. The motor can be enabled to apply a physical force, directly or indirectly, to the storage device. The physical force applied can promote and generate various movement(s) of the storage device, including any contents therein, such as a rotational, stirring, vibrational (oscillatory) and other movements as may be contemplated. It is contemplated that various additional component features may comprise a 1-MCP generator and provide various capabilities, such as enabling the connection and/or removable connection of the operation of the motor to the storage device, as may be contemplated by those skilled in the art without departing from the scope and spirit of the present invention.

For the contemplated and preferred embodiments, the device can be a storage device, mixing tank and the like, that may be configured as a container, vessel or other suitable structure as contemplated by those skilled in the art. Within the storage device the carrier complex can be placed and/or positioned for storage, handling and/or processing. Within the storage device direct or indirect interaction with water, preferably de-ionized and distilled water, by the carrier complex can be enabled and further promote the controlled release of the 1-MCP gas from the carrier complex. Connection of the storage device to the force generation mechanisms of a 1-MCP generator, such as to a motor or an electromagnetic element (i.e., electromagnetic coil), can promote and enable the application of a physical force to the carrier complex (1-MCP+carrier) and/or mixture (release mixture), via its being contained within the storage device.

Additional component features of a 1-MCP generator for the current invention can comprise various mechanisms and/or systems, such as a control mechanism(s), heating mechanism(s), ventilation mechanism(s) and the like as may be contemplated. For example, in exemplary embodiments, a control system such as a programmable relay cycle timer can provide a user determinable capability, such as setting a delay for the start of operation of the 1-MCP generator and various other mechanisms and/or systems. The control system can provide for a delay or the time lag ranging from 1 second (1 s) to 21 days, preferably from 5 s to 15 days, more preferably from 10 s to 10 days. In exemplary embodiments, a ventilation system can be provided, such as a small window on the lid of the generator, a ventilation fan and the like as may be contemplated.

In still further exemplary embodiments, a heating mechanism/system can provide the means for heating certain aspects or components of a 1-MCP generator, preferably providing heat to a device and/or heating water that is present in the 1-MCP generator to accomplish the generation of steam from heating of the water. The heating mechanism/system in contemplated embodiments can be provided, at least in part, as a heating element, heating plate, heating coil and/or heating chamber that is operationally connected with a water reservoir in the 1-MCP generator, wherein heat can be applied to water contained in the water reservoir. The interaction of steam with the carrier complex can range from 5 minutes to 48 hours, 20 minutes to 5 hours, more preferably from 30 minutes to 2 hours. It is further contemplated that any exemplary 1-MCP generator can comprise multiple accessories for convenience and monitoring. Such accessories can comprise various transportation mechanisms, such as wheels and a handle for easy transportation of the equipment, a 1-MCP monitoring system, a small container for placing 1-MCP/carrier complex and like as may be contemplated.

Prior to the release of 1-MCP in gas form, the 1-MCP is and can be stored, at least temporarily, as part of or in what is referred to as a "carrier complex" and/or "complexed 1-MCP", wherein the 1-MCP is trapped or complexed into selective solid matrices or carrier materials, referred to herein as "carrier(s)", "agent(s)", "encapsulant(s)", and/or "adsorbent(s)", as described herein. For the current invention, the means of promoting the release of the 1-MCP gas from the carrier complex can be achieved in various ways and preferably through application of a physical force. It is further contemplated that the release of the complexed 1-MCP gas is promoted by mixing it in a liquid, preferably de-ionized and distilled water, and/or exposing it to steam. A significant advantage and improvement provided by the embodiments for the current invention is in accomplishing the release of 1-MCP gas from a carrier complex by the direct or indirect application of a physical force, mixing the carrier complex in water and/or exposing the carrier complex to water vapor interaction, all of which promotes the release of the 1-MCP gas from the carrier complex, through dissociation from the carrier, with a desirable (compliant) impurity profile. In addition, the release of 1-MCP gas occurs in conjunction with the foam avoidance capabilities of the current invention, whereby, the release process(es) promote the reduction and/or avoidance of the generation of foam by-product and any of its associated, unwanted effects as have been described herein.

For contemplated and preferred embodiments of the current invention, a 1-MCP generator provides for the mixing of a 1-MCP/carrier complex (carrier complex) in water, thereby establishing a mixture (as previously identified as being referred to herein as the "clean mixture", "release mixture" or "complex mixture"). The generator further provides a mechanism for the application of a physical force (referred to herein as a "release force" or "releasing force") to promote the mixing and/or agitation of the complex mixture which promotes and can achieve the dissociation and/or release of 1-MCP from the carrier in the carrier complex, thereby allowing the 1-MCP to be released in a gaseous form.

Carriers that are contemplated for use by the current invention for 1-MCP include, without limitation, an encapsulant(s) and/or adsorbent(s), preferably α-cyclodextrin, metal organic framework, zeolites, activated carbons, cucurbit[6]uril, and other polymeric or porous materials such as gelatin and pectin, including any contemplated derivatives thereof. The carrier (1-MCP) complex can be placed directly into the generator, or it can be contained in various packages and water permeable materials, such as water soluble and/or dissolvable polyvinyl alcohol pouch, water soluble and/or dissolvable paper bag, and various other water soluble or water dissolvable or water vapor permeable containers, storage devices, films or pouches as may be contemplated, such as various commercially available (i.e., Tyvek™) pouch and/or film.

In preferred embodiments of this invention any physical means and mechanisms that promote the mixing/agitation of 1-MCP/carrier complex in water are contemplated for use. Typical physical means (release force(s)) include rotation, stirring, and vibration, preferably rotation and stirring. Rotation refers to a circular movement of an object, such as a rotating element moving around a fixed axis and the like as may be contemplated by those skilled in the art, around a center (or point) of rotation. It is contemplated that the rotational (release) force can be provided through the movement of the mixing tank (rotating element) around a fixed axis. Stirring refers to moving an object around in a liquid or other substance in order to mix it thoroughly. For embodiments of the current invention, a stirring (release) force can refer to the movement of a magnetic stir bar or a mixing rod with or without one or more propellers in the liquid. Vibration refers to a mechanical phenomenon whereby oscillations occur about an equilibrium point. For embodiments of the current invention vibration can mean oscillation of the mixing tank or the liquid inside the tank.

In preferred embodiments of the current invention, the 1-MCP generator can comprise a mechanical motor to provide the power for promoting and/or generating a releasing force, such as a rotation force. The motor can be powered by direct current or alternating current. The motor can have rpm ranges from 15-50000 rpm, preferably 15-30000 rpm, more preferably 15-20000 rpm. The torque ranges from 0.0001 to 300 Nm, preferably 0.0002 to 100 Nm, more preferably 0.0002 to 50 N·m. The operation time can range from 5 minutes to 48 hours, preferably from 5 hours to 30 hours, more preferably from 10 hours to 24 hours. The operation can be continuous or intermittent. In the case of intermittent rotation, the total time for which a rotational force is being applied and mixing provided can range from 5 minutes to 48 hours, preferably from 5 hours to 30 hours, more preferably from 10 hours to 24 hours. The intermittent rotation is controlled by a control system such as a programmable relay cycle timer. The intermittent operation can be more cost and energy-effective than continuous operation and can sustain longer treatment (mixing) time.

As described herein, it is contemplated for preferred embodiments of the current invention to use a vessel, container, storage device and/or mixing tank, that may also be referred to herein as a reaction vessel, that can be variously configured, sized and be constructed of various materials, such as a plastic or metal mixing tank. The shape of the tank can be varied depending on, including but not limited to, cost, convenience, volume of liquid(s), application room size. If plastic is used, use of nylon, polyethylene terephthalate, polypropylene, and high density polyethylene is preferred; if metal is used, use of stainless steel for food processing application is preferred. The mixing tank can be fixed within the generator, or it can be removable from the generator for easy cleaning after application. The volume of the tank can range from 10 mL to 100 L, preferably from 20 mL to 80 L, more preferably from 50 mL to 60 L.

In preferred embodiments, a releasing force, such as a rotational force that can be applied by an exemplary 1-MCP generator can provide for the rotation of the mixing tank in two (2) dimensions. Rotation in two (2) dimensions refers to the path taken by the mixing tank, wherein the mixing tank follows a circular path and the mixing tank can be established either in a horizontal or vertical relationship to a determined planar surface. The rotation is created by a mechanical motor, which can be powered by direct or alternating current. The speed of rotation can be 15-50000 rpm, preferably 15-30000 rpm, more preferably 15-20000 rpm. To promote increased mixing of objects and/or materials within the mixing tank, mixing aids such as bearing balls can be placed in the mixing tank. The bearing ball(s) can be placed freely in the tank or its moving path can be fixed. One or multiple bearing balls can also be used in the mixing tank, preferably 1 to 20, more preferably 2 to 15. The rotation can be continuous or intermittent. The operation time can range from 5 minutes to 48 hours, preferably from 5 hours to 30 hours, more preferably from 10 hours to 24 hours. The intermittent rotation can be controlled by a control system such as a programmable relay cycle timer. The intermittent operation can be more cost and energy-effective than continuous operation and can sustain longer treatment time.

In preferred embodiments of the current invention, the releasing force can be a rotational force that can be applied by an exemplary 1-MCP generator and can provide for the rotation of the mixing tank in three (3) dimensions. Rotation in three (3) dimensions refers to the path taken by the mixing tank as being a gyratory path with a tilted angle from a flat (planar) surface. As such, in this embodiment, the mixing tank is both established at a tilted angle relative to the planar surface and follows a circular path either in a substantially horizontal or vertical relationship to the planar surface in relation to the tilted-angle. The speed of rotation can be 15-50000 rpm, preferably 15-30000 rpm, more preferably 15-20000 rpm. The tilt angle can be 5°-60°, preferably 5°-50°, more preferably 5°-30°. It is understood that the tilt angle, for any exemplary and contemplated embodiments herein, can be established in relationship to any significantly horizontal or vertical plane, desired path or other feature of a generator. To promote increased mixing effectiveness, mixing aids such as bearing balls can be placed in the mixing tank. The bearing ball can be placed freely in the tank or its moving path can be fixed. One or multiple bearing balls can also be used in the mixing tank, preferably 1 to 20, more preferably 2 to 15. It is contemplated that one or more mixing aids, such as the bearing balls and the like, may be employed with any of the embodiments of the current invention. The rotation can be continuous or intermittent. The operation time can range from 5 minutes to 48 hours, preferably from 5 hours to 30 hours, more preferably from 10 hours to 24 hours. The intermittent rotation can be controlled by a control system such as a programmable relay cycle timer. The intermittent operation can be more cost and energy-effective than continuous operation, and can sustain longer treatment time.

Preferred exemplary embodiments of the current invention can provide a releasing force, such as a stirring force, created by a motor. The motor can be powered by direct current or alternating current. The motor can have rpm ranges from 15-50000 rpm, preferably 15-30000 rpm, more preferably 15-20000 rpm. The torque can range from 0.0001 to 300 Nm, preferably 0.0002 to 100 Nm, more preferably 0.0002 to 50 N·m. The operation time can range from 5 minutes to 48 hours, preferably from 5 hours to 30 hours, more preferably from 10 hours to 24 hours. The operation can be continuous or intermittent. In the case of intermittent rotation, the total time of mixing/agitation can range from 5 minutes to 48 hours, preferably from 5 hours to 30 hours, and more preferably from 10 hours to 24 hours. The stirring rod can have one to multiple stirring blades, propellers and the like, preferably 1 to 10, more preferably 1 to 4. The stirring rod can rotate around a fixed axis or around a fixed point.

Any stirring mechanism providing stirring movement around a fixed point, as may be contemplated by and as has been described herein for exemplary embodiments of the current invention, can promote larger surface area covered by stirring. The surface area is dependent on the length of the stirring rod, the volume of the water, and the size of the mixing tank. The covered stirring surface area can range from 10% to 100%, or 50%-100% of the surface area of the mixing tank. The stirring can also be realized using a magnetic stir bar which can be accomplished and/or driven by magnetic coupling attached on the motor. In preferred embodiments, that attached magnetic coupling can be enabled through the use of an electromagnetic element, such as an electromagnetic coil or other mechanisms and devices as are known by those skilled in the art. The stir bar can rotate around a fixed axis or around a fixed point. Stirring around a fixed point can promote larger surface area covered by stirring. The surface area is dependent on the length of the stir bar, the volume of the water, and the size of the mixing tank. The covered stirring surface area can range from 10% to 100%, or 50%400% of the surface area of the mixing tank. The stirring provided by exemplary embodiments of the current invention can be continuous or intermittent. The operation time can range from 5 minutes to 48 hours, preferably from 5 hours to 30 hours, more preferably from 10 hours to 24 hours. The intermittent rotation can be controlled by a control system such as a programmable relay cycle timer. The intermittent operation can be more cost and energy-effective than continuous operation, and can sustain longer treatment time.

Preferred exemplary embodiments of the current invention can provide a releasing force, such as a stirring force, created by an electromagnetic element. The electromagnetic element can be a device or mechanism, such as an electromagnetic coil or other similar device or mechanism as contemplated by those skilled in the art, and can be powered by direct current or alternating current. The electromagnetic coil can generate the stirring of a magnetic stir bar with rpm ranges from 15-50000 rpm, preferably 15-30000 rpm, more preferably 15-20000 rpm. The operation time can range from 5 minutes to 48 hours, preferably from 5 hours to 30 hours, more preferably from 10 hours to 24 hours. The operation can be continuous or intermittent. In the case of intermittent rotation, the total time of mixing/agitation can range from 5 minutes to 48 hours, preferably from 5 hours to 30 hours, and more preferably from 10 hours to 24 hours. The stir bar can rotate around a fixed axis or around a fixed point. Stirring around a fixed point can promote larger surface area covered by stirring. The surface area is dependent on the length of the stir bar, the volume of the water, and the size of the mixing tank. The covered stirring surface area can range from 10% to 100%, or 50%-100% of the surface area of the mixing tank. The stirring can be continuous or intermittent. The operation time can range from 5 minutes to 48 hours, preferably from 5 hours to 30 hours, more preferably from 10 hours to 24 hours. The intermittent rotation can be controlled by a control system such as a programmable relay cycle timer. The intermittent operation can be more cost and energy-effective than continuous operation, and can sustain longer treatment time.

In additional exemplary embodiments of the current invention, a 1-MCP generator can provide multiple capabilities. Multiple capabilities can refer to the force generation and application capabilities enabled for and by the 1-MCP generator. It is contemplated that an exemplary 1-MCP generator can be configured and enabled to provide for the generation and application of multiple releasing forces, such as both a rotation and stirring force, thereby generating both a rotation and stirring movement for the mixing tank and/or the contents therein. Alternatively, the generator can be configured to apply one or more releasing (physical) forces in conjunction with promoting the generation and interaction of water vapor (steam) with a carrier complex. For example, a 1-MCP generator can be variously configured and provide both a 2-dimension or 3-dimension rotation to a mixing tank and an overhead stirring mechanism, to promote the movement of a mixture in the mixing tank and release of 1-MCP gas from complex. By way of example, for 3-dimension embodiments, a tilt-angle relative to a planar surface can range from 5°-60°, preferably 5°-50° and more preferably 5°-30°. The speed of the rotation of the mixing tank or the stirring rod, and the time taken for complete release of 1-MCP depends on any number of different factors, including but not limited to, volume of the liquid in the tank, size of the enclosed application area, amount of the 1-MCP/carrier complex in the mixture and type of the carrier.

It is contemplated that the exemplary 1-MCP generator(s) embodied for the current invention enables a delayed release of 1-MCP gas through the application of a physical (releasing) force(s) (e.g., rotation or stirring), and/or other means. The delay capability provided is another practical and advantageous feature because it promotes the reduction and/or minimization of the risk that a 1-MCP generator operator can be exposed to any released 1-MCP gas. In operation, to achieve release of the 1-MCP gas utilizing any of the exemplary 1-MCP generator embodiments of the current invention, the 1-MCP/carrier complex is placed in the 1-MCP generator (a.k.a., container, receptacle, storage device, mixing tank) which is located inside the application area (i.e., a room, packing and holding area or other suitable location) by a trained operator. The generator, in some cases, is designed to start working once the operator leaves the application area. In exemplary embodiments of this invention, a control (timing) system can be used to allow an operator to determine (delay) the timing of the start of operation of the 1-MCP generator, such as the generation and application of a rotation or stirring force. Such a control system can allow an operator to determine (delay) the start of operation of the generator to promote operational safety. For instance, the control system can allow the operator to delay the start of operation for such a determinable time period as to account for any time required for the placement of 1-MCP/carrier complex in the generator till the operator leaves the application area and safely closes or seals the application area. This can advantageously promote the reduction and minimization of the risk that an operator can be exposed to any released 1-MCP gas. Also, the delay capability can also provide the growers and packers with convenient options for multiple 1-MCP treatments; for example, multiple generators can be placed in a treatment area in which some generators operate to provide the first treatment and some generators operate to provide the second treatment after a few days. The control system can provide for a delay or the time lag ranging from 1 second (1 s) to 21 days, preferably from 5 s to 15 days, more preferably from 10 s to 10 days. The delayed operation can be achieved by delaying the rotation or stirring operation, or by delaying the opening of a ventilation system in a generator. A ventilation system can be a small window on the lid of the generator, a ventilation fan or such other mechanisms and devices as are known by those skilled in the art. By way of example, the delayed operation of the 1-MCP generator and/or any of its systems can be achieved by a control system such as a programmable relay cycle timer.

A preferred embodiment of a 1-MCP generator 100 is shown in FIG. 1. It is contemplated that preferred method and system embodiments for the current invention can be performed at least in part and/or accomplished utilizing the 1-MCP generator 100 shown in FIG. 1. This embodiment provides a two dimensional rotation 1-MCP generator 100 comprising a removable mixing tank 107 with total volume of 20 L, two ventilation fans 104, a mechanical motor 103 connected to the mixing tank through a holding platform (receptacle) 101 for the mixing tank, a cover 102 for the motor, two wheels 106, and a control panel 105 that controls the on and off of the generator, and operation time of the ventilation fan. The motor imparts a rotation speed of 50 rpm.

Figure 2:
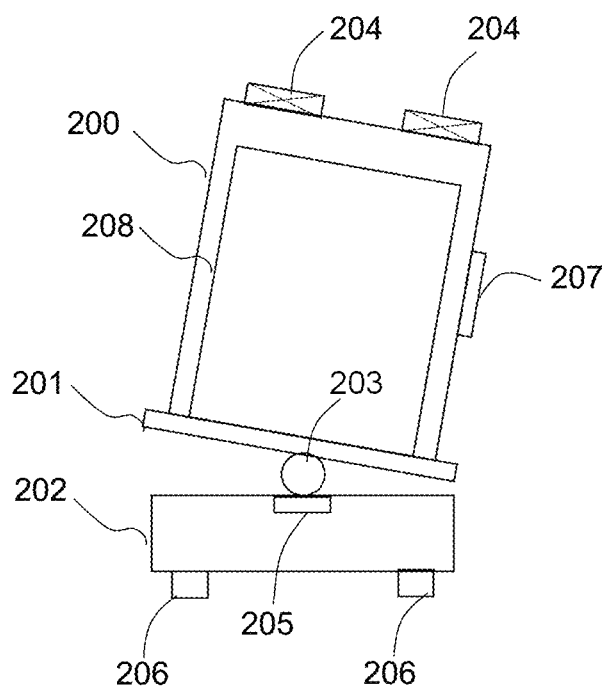
FIG. 2 is an illustration of a three dimensional rotational motion 1-MCP generator in accordance with the current invention.

A preferred embodiment of a 1-MCP generator 200 is shown in FIG. 2. It is contemplated that preferred method and system embodiments for the current invention can be performed at least in part and/or accomplished utilizing the 1-MCP generator 200 shown in FIG. 2. This embodiment provides a three dimensional rotation 1-MCP generator 200 comprising a removable mixing tank 208 with total volume of 20 L, two ventilation fans 204, a mechanical motor 205 connected to the mixing tank through a holding platform (receptacle) 201, and a round shape rotation support 203, a cover for motor 202, two wheels 206, and a control panel 207 that controls the on and off of the generator, and operation time of the ventilation fan. The motor has a rotation speed of 20 rpm, and a tilt angle of 15°.

Figure 3:
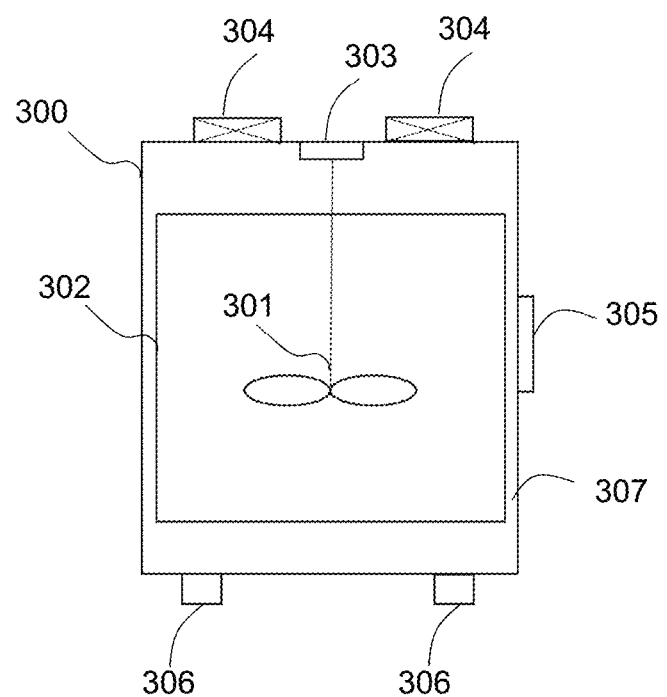
FIG. 3 is an illustration of a stirring motion 1-MCP generator in accordance with the current invention.

A preferred embodiment of a 1-MCP generator 300 is shown in FIG. 3. It is contemplated that preferred method and system embodiments for the current invention can be performed at least in part and/or accomplished utilizing the 1-MCP generator 300 shown in FIG. 3. This embodiment provides a stirring 1-MCP generator 300 comprising a receptacle 307 configured to removably connect with a removable mixing tank 302, with total volume of 20 L, two ventilation fans 304, a mechanical motor 303 attached on the lid of the generator, a stirring rod with propeller 301 attached on the motor, two wheels 306, and a control panel 305 that controls the on and off of the generator, and operation time of the ventilation fan. The motor has a rotation speed of 200 rpm.

Figure 4:
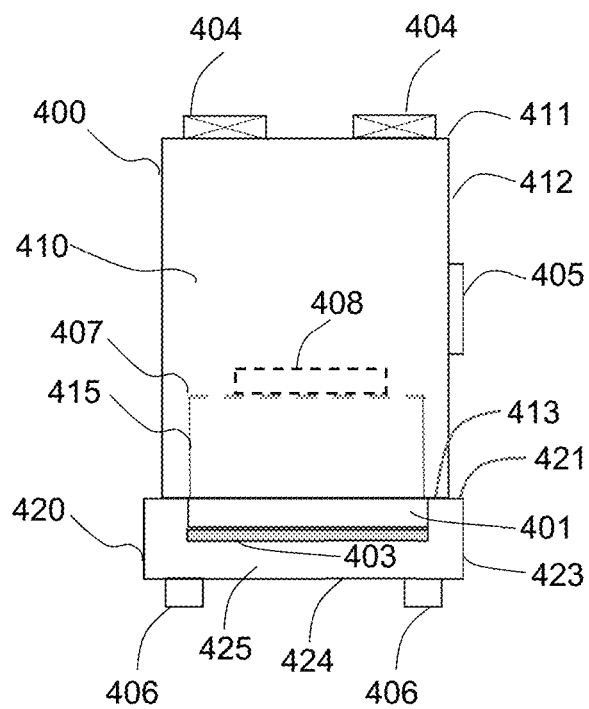
FIG. 4 is an illustration of a steam 1-MCP generator in accordance with the current invention.

A preferred embodiment of a 1-MCP generator 400, also referred to herein as a "steaming generator" or "separator generator", is shown in FIG. 4. It is contemplated that preferred method and system embodiments for the current invention can be performed at least in part and/or accomplished utilizing the 1-MCP generator 400 shown in FIG. 4. This embodiment provides a steaming 1-MCP generator 400 comprises a housing 410 that is removably connected to a base unit 420. Housing 410 is defined by a top 411 connected to walls 412 having an open bottom edge 413. Two ventilation fans 404 are positioned within top 411. A control panel 405, that controls the on and off capabilities of the generator, and operation time of the ventilation fan, is positioned within wall 412 between the top 411 and bottom edge 413. An interior space of housing 410 is defined by a receptacle 415 within which a mesh screen stand 407 can be positioned in removable connection with top side 421 of base unit 420. Preferably, the mesh screen stand 407 is positioned within the receptacle 415 and above the base receptacle 420. The mesh screen stand 407, also referred to herein as a "separator", allows for a carrier complex (including 1-MCP) to be placed on a top platform 408 which also allows the carrier complex to remain entirely separated from the water contained in water reservoir 401. Preferably the top platform 408 is configured, at least in part, with or as a perforated surface, such as a variously configured mesh pattern, thereby, providing openings that allow for gases and vapors, such as steam (water vapor), to pass through and interact with materials that are positioned upon the top platform 408.

Base unit 420 has a top side 421 defined by walls 423 and a bottom side 424. Two wheels 406 are connected to and extend from the bottom side 424. Positioned entirely within an interior space 425 of base unit 420, is a heating element 403, in this preferred embodiment the heating element 403 is a heating plate, enabled to be in operational connection with a water reservoir 401. Water can be stored and handled within water reservoir 401 and heat can be applied to the water, for the purpose of generating steam, by heating element (plate) 403.

Utilizing 1-MCP generator 400, the generation and/or release of 1-MCP gas from the carrier complex can be achieved through interaction between the carrier complex and water vapor (steam) in the 1-MCP generator. Steam, in this context, refers to the vapor phase of water. In preferred embodiments of the current invention a 1-MCP generator can employ the use of steam to release 1-MCP gas. In exemplary embodiments, the 1-MCP generator is configured such that the 1-MCP/carrier complex is not allowed to come in direct contact with water. The generator includes a water reservoir and a heating element, such as a heating coil or other heating mechanism or device, separated from the carrier complex, wherein the heating element is capable of heating the water to transition the water into a vapor phase, such as by reaching the boiling point and, thereby, generating the steam. The volume of water reservoir ranges from 5 mL to 60 L, preferably from 6 mL to 50 L, more preferably from 8 mL to 30 L. The reservoir can be removable for easy filling and cleaning. The steam that is generated, when it comes in contact with the carrier of the 1-MCP/carrier complex, significantly promotes the dissociation of 1-MCP gas from the carrier, and thereby release of the 1-MCP in gas form. The heating of water in the reservoir can be accomplished via any heating element, mechanism or device, such as a heating coil or heating chamber, which can be powered by direct current, alternating current, or gas. The steam temperature can range from 90° C. to 500° C., preferably 95° C. to 400° C. and more preferably 100° C. to 350° C. The water reservoir is separated from the 1-MCP/carrier complex in the generator to prevent direct contact. The separator is preferably perforated to allow steam to come in contact with 1-MCP/carrier complex. It is contemplated that a blower mechanism, such as a blower or fan, may be connected to a 1-MCP steam generator to circulate steam within a generator housing to promote the interaction with the complex carrier and/or push steam or released 1-MCP gas out of a generator housing. The interaction of steam with the carrier complex can range from 5 minutes to 48 hours, 20 minutes to 5 hours, more preferably from 30 minutes to 2 hours.

It is contemplated that an exemplary 1-MCP steam generator for the current invention can provide multiple capabilities, such as multiple releasing forces and others as may be contemplated. For instance, it can be configured with mechanisms that enable it to generate and apply both a physical force/movement and steam. By way of example, utilizing generator 400 from FIG. 4 as a reference, the mesh screen stand 407 can be replaced with a mixing tank that is appropriately configured to provide for the storage of a mixture, such as water mixed with the carrier complex. The mixing tank allowing for interaction with the steam generated by the heating of the water in the water reservoir 401. The mixing tank further allowing for a stirring mechanism, such as a multi-bladed propeller device to be inserted into the mixture. The multi-bladed propeller device being able to generate a rotational movement in the mixture by its operational connection with a motor that applies a rotational force to the device. It is contemplated that the stirring mechanism could be removably mounted and repositioned in its mounting location within the top 411 and the connection to the motor, which may also be mounted to 411, could be made through various means as known to those skilled in the art to enable the desired operation. The control panel 405 can control various operational capabilities of the generator, such as control over the operation of the motor, such as on/off, an operational timing and such other capabilities as may be contemplated.

FIG. 5 is a preferred method 500 embodiment of the current invention for generating and releasing a 1-MCP gas. In a step 510, establishing a mixture comprising a carrier complex in water within an interior space of a mixing tank. In step 520 releasing a gaseous form of 1-MCP from the carrier complex by the application of a releasing force provided through connection of the mixing tank to a motor. The process of releasing 1-MCP gas in the current embodiment can further provide a desirable foam by-product profile by promoting the reduction and/or avoidance of foam by-product generation and can promote formation of a compliant impurity profile for the released 1-MCP gas in accordance with the current invention. This method 500 providing for greater than 96%, more preferably 100%, of 1-MCP gas being released from the carrier complex. The amount of carrier complex ranges from 0.001 kg to 10 kg, preferably 0.01 kg to 6 kg and more preferably 0.02 kg to 1 kg and the ratio of carrier complex to water ranges from 1:500 to 1:5 and more preferably 1:100 to 1:10. The carrier complex can be placed directly into the water in the interior space of the mixing tank or, at least initially, indirectly placed into contact with the water in the mixing tank by being contained in at least one of a water soluble and/or dissolvable polyvinyl alcohol pouch, water soluble and/or dissolvable paper bag and various other water soluble and/or dissolvable containers, films or pouches as may be contemplated. The carrier that can be complexed with 1-MCP to form the carrier complex can comprise one or more of an encapsulant(s) and/or adsorbent(s), preferably α-cyclodextrin, metal organic framework, zeolites, activated carbons, cucurbit[6]uril, and other polymeric or porous materials such as gelatin and pectin.

The generator provides a mechanism which can apply the releasing force during an operation time to the mixture in the mixing tank, said releasing force comprising at least one of a rotational, stirring, shaking and/or vibratory (oscillatory) force, in at least one of a continuous or intermittent manner. The application of the releasing force can also be determined in one or more of two and three dimensions and wherein the mixing tank can be tilted at an angle relative to a planar surface, such as the holding plate as described in FIG. 2. The speed of rotation imparted to the mixing tank can be at least one of 15-50000 rpm, preferably 15-30000 rpm and more preferably 15-20000 rpm. Where a stirring mechanism is employed it may comprise a stirring rod comprising stirring propellers, preferably 1 to 10, more preferably 1 to 4 and/or a magnetic stir bar with stirring speed of 15-50000 rpm, preferably 15-30000 rpm and more preferably 15-20000 rpm. Where a gyratory movement is desired to be generated, the mixing tank can be established at a tilt angle relative to a horizontal planar surface. The tilt-angle relative to the planar surface can range from 5°-60°, preferably 5°-50° and more preferably 5°-30°. The 1-MCP generator employed for accomplishing the method 500 can provide a tortious (torque) force ranges from 0.0001 to 300 Nm, preferably 0.0002 to 100 Nm, more preferably 0.0002 to 50 N·m. It is also contemplated that the operation time can range from 5 minutes to 48 hours, preferably from 5 hours to 30 hours, more preferably from 10 hours to 24 hours. The method 500 may also employ the use of one or more mixing aids that can be positioned freely or their moving path can be fixedly established in the interior space of the mixing tank, wherein the mixing aids can comprise at least one of bearing balls ranging in number from 1 to 20 and more preferably 2 to 15. The mixing tank volume can range from 10 mL to 100 L, preferably from 20 mL to 80 L, more preferably from 50 mL to 60 L and the volume of water in the mixing tank can range from 9 mL to 99 L, preferably 19 mL to 79 L and more preferably 29 mL to 59 L.

Figure 6:
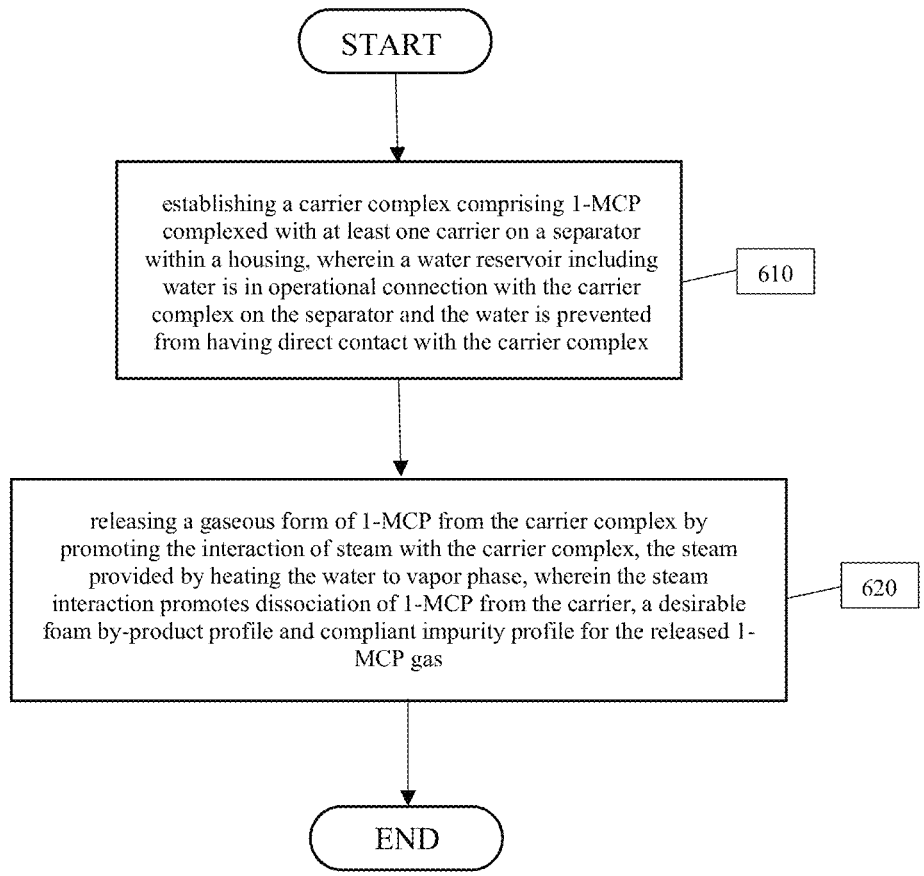
FIG. 6 is a block diagram illustrating a second preferred method for releasing a 1-MCP gas in accordance with an exemplary embodiment of the current invention.

FIG. 6 is a preferred method 600 embodiment of the current invention for generating and releasing a 1-MCP gas. In step 610 establishing a carrier complex comprising 1-MCP complexed with at least one carrier on a separator within a housing, wherein a water reservoir including water is in operational connection with the carrier complex on the separator and the water is prevented from having direct contact with the carrier complex. In step 620 releasing a gaseous form of 1-MCP from the carrier complex by promoting the interaction of steam with the carrier complex, the steam provided by heating the water to vapor phase. The process of releasing 1-MCP gas in the current embodiment can further provide a desirable foam by-product profile by promoting the reduction and/or avoidance of foam by-product generation, and can promote formation of a compliant impurity profile for the released 1-MCP gas in accordance with the current invention. This method 600 providing for greater than 96%, more preferably, significantly 100%, of 1-MCP gas being released from the 1-MCP/carrier complex. The steam temperature ranges from 90° C. to 500° C., preferably 95° C. to 400° C. and more preferably 100° C. to 350° C. The amount of carrier complex ranges from 0.001 kg to 10 kg, preferably 0.01 kg to 6 kg and more preferably 0.02 kg to 1 kg and the ratio of carrier complex to water ranges from 1:500 to 1:5 and more preferably 1:100 to 1:10. The carrier complex can be placed in a water soluble and/or dissolvable polyvinyl alcohol pouch, water soluble and/or dissolvable paper bag and various other water soluble and/or dissolvable or water vapor permeable containers or pouches as may be contemplated. The carrier that can be complexed with 1-MCP to form the carrier complex can comprise one or more of an encapsulant(s) and/or adsorbent(s), preferably α-cyclodextrin, metal organic framework, zeolites, activated carbons, cucurbit[6]uril, and other polymeric or porous materials such as gelatin and pectin.

Figure 7:
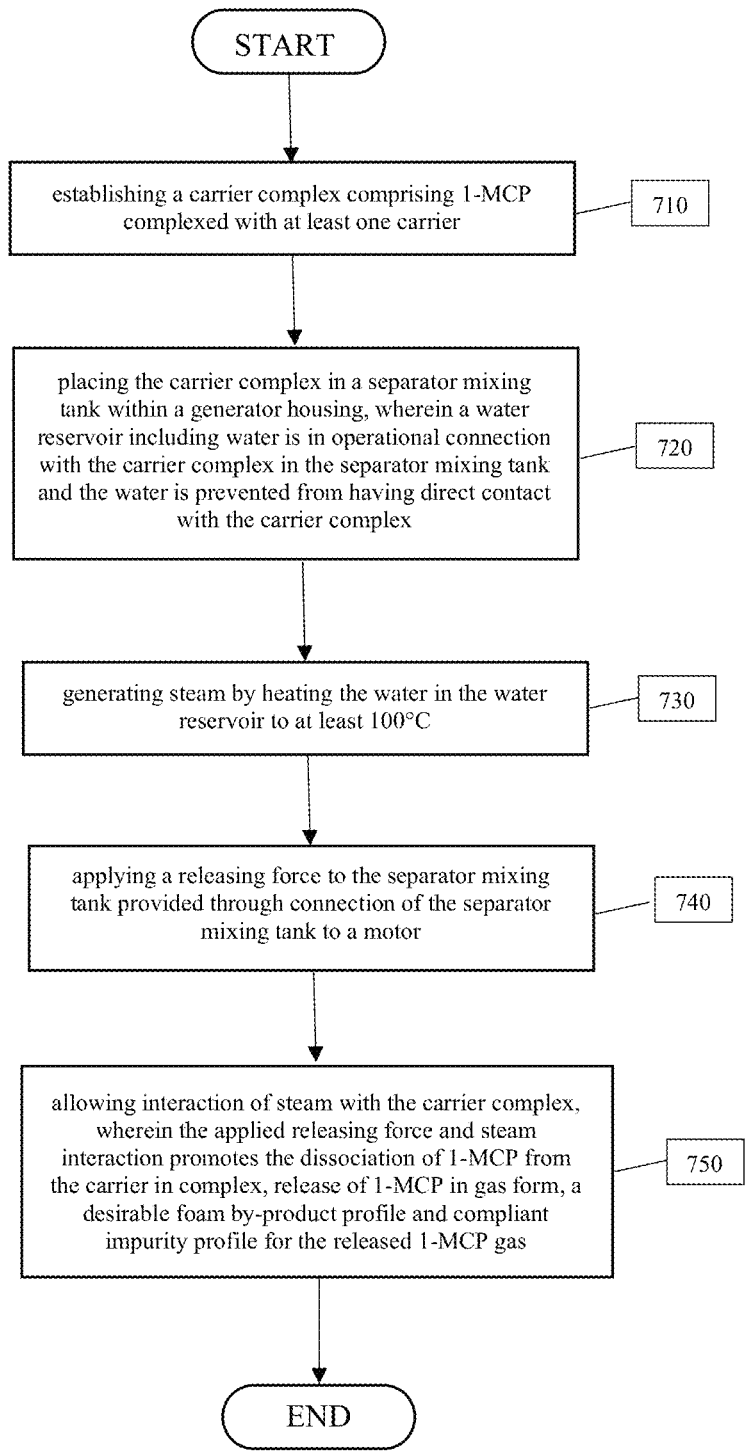
FIG. 7 is a block diagram illustrating a third preferred method for releasing a 1-MCP gas in accordance with an exemplary embodiment of the current invention.

FIG. 7 is a preferred method 700 embodiment of the current invention for generating and releasing a 1-MCP gas. In step 710 establishing a carrier complex comprising 1-MCP complexed with at least one carrier. In step 720 placing the carrier complex in a separator mixing tank within a generator housing, wherein a water reservoir including water is in operational connection with the carrier complex in the separator mixing tank and the water is prevented from having direct contact with the carrier complex. In step 730 generating steam by heating the water in the water reservoir to at least 100° C. The steam temperature can range from 90° C. to 500° C., preferably 95° C. to 400° C. and more preferably 100° C. to 350° C. In step 740 applying a releasing force to the separator mixing tank provided through connection of the separator mixing tank to a motor. In step 750 allowing interaction of steam with the carrier complex, wherein the applied releasing force and steam interaction promotes the dissociation of 1-MCP from the carrier in complex and release of 1-MCP in gas form. It is contemplated that the application of the releasing force and steam interaction can be significantly concurrent and/or in a sequential manner as may be contemplated without departing from the scope and spirit of the current invention. The process of releasing 1-MCP gas in the current embodiment can further provide a desirable foam by-product profile by promoting the reduction and/or avoidance of foam by-product generation, and can promote formation of a compliant impurity profile for the released 1-MCP gas in accordance with the current invention.

Figure 8:
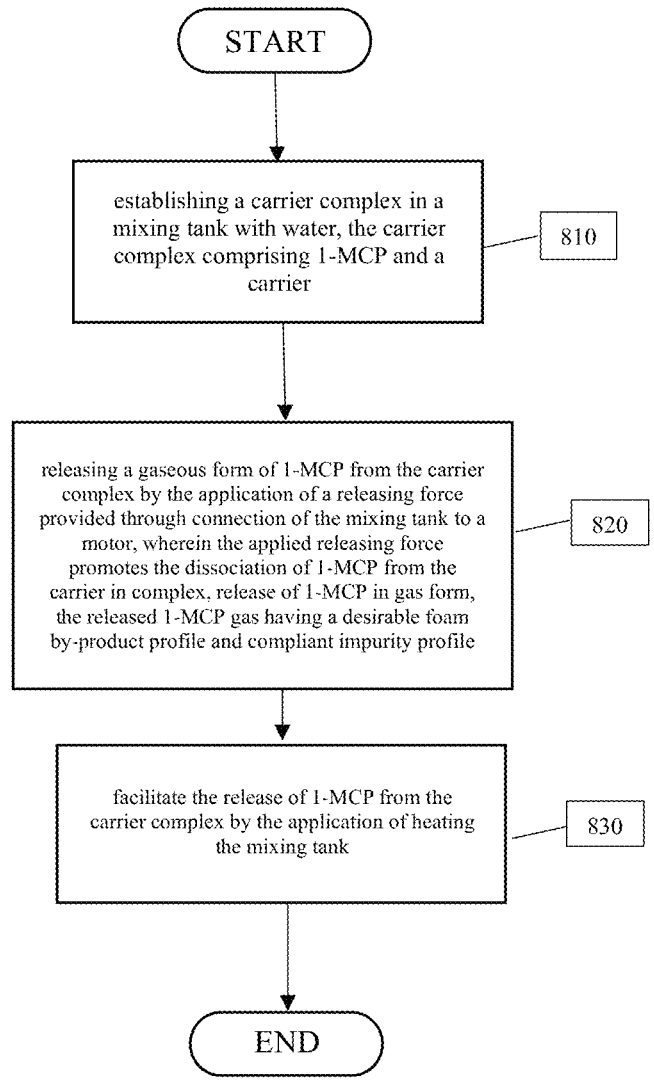
FIG. 8 is a block diagram illustrating a fourth preferred method for releasing a 1-MCP gas in accordance with an exemplary embodiment of the current invention.

FIG. 8 is a preferred method 800 embodiment of the current invention for generating and releasing a 1-MCP gas. In a step 810, establishing a carrier complex comprising 1-MCP complexed with at least one carrier in an interior space of a mixing tank including water. The amount of carrier complex ranges from 0.001 kg to 10 kg, preferably 0.01 kg to 6 kg and more preferably 0.02 kg to 1 kg and the ratio of carrier complex to water ranges from 1:500 to 1:5 and more preferably 1:100 to 1:10. In step 820 releasing a gaseous form of 1-MCP from the carrier complex by the application of a releasing force provided through operational connection of the mixing tank to a motor. The process of releasing 1-MCP gas in the current embodiment can further provide a desirable foam by-product profile by promoting the reduction and/or avoidance of foam by-product generation, and can promote formation of a compliant impurity profile for the released 1-MCP gas in accordance with the current invention. In step 830 the water in the mixing tank is heated to vapor phase, thereby generating steam, via a heating coil or heating chamber, which is powered by direct current, alternating current, or gas. The water temperature for at least portion of the 1-MCP Release Process can range from 30° C. to 100° C., preferably 30° C. to 80° C. and more preferably 40° C. to 60° C. The interaction of steam during the release of the 1-MCP gas promotes method 800 providing for greater than 96%, more preferably 100%, of 1-MCP gas being released from the carrier complex. It is further contemplated that steam may interact with the gaseous form of 1-MCP that is released by the applied releasing (physical) force provided in step 820, which also promotes the percentage release of 1-MCP gas as described above. Thus, the current invention, by enabling a significantly concurrent or sequential application of a releasing force and steam interaction can provide a desirable foam by-product profile and compliant impurity profile.

The carrier complex can be placed directly into the water in the interior space of the mixing tank or, at least initially, indirectly placed into contact with the water in the mixing tank by being contained in at least one of a water soluble and/or dissolvable polyvinyl alcohol pouch, water soluble and/or dissolvable paper bag and various other water soluble and/or dissolvable containers, films or pouches as may be contemplated. The carrier that can be complexed with 1-MCP to form the carrier complex can comprise one or more of an encapsulant(s) and/or adsorbent(s), preferably α-cyclodextrin, metal organic framework, zeolites, activated carbons, cucurbit[6]uril, and other polymeric or porous materials such as gelatin and pectin. The generator provides a mechanism which can apply the releasing force during an operation time to the mixture in the mixing tank, said releasing force comprising at least one of a rotational, stirring, shaking and/or vibratory (oscillatory) force, in at least one of a continuous or intermittent manner. The application of the releasing force can also be determined in one or more of two and three dimensions and wherein the mixing tank can be tilted at an angle relative to a planar surface, such as the holding plate as described in FIG. 2. The speed of rotation imparted to the mixing tank can be at least one of 15-50000 rpm, preferably 15-30000 rpm and more preferably 15-20000 rpm. Where a stirring mechanism is employed it may comprise a stirring rod comprising stirring propellers, preferably 1 to 10, more preferably 1 to 4 and/or a magnetic stir bar with stirring speed of 15-50000 rpm, preferably 15-30000 rpm and more preferably 15-20000 rpm. Where a gyratory movement is desired to be generated, the mixing tank can be established at a tilt angle relative to a horizontal planar surface. The tilt-angle relative to the planar surface can range from 5°-60°, preferably 5°-50° and more preferably 5°-30°. The 1-MCP generator employed for accomplishing the method 800 can provide a tortious (torque) force ranges from 0.0001 to 300 Nm, preferably 0.0002 to 100 Nm, more preferably 0.0002 to 50 N·m. It is also contemplated that the operation time can range from 5 minutes to 48 hours, preferably from 5 hours to 30 hours, more preferably from 10 hours to 24 hours. The method 800 may also employ the use of one or more mixing aids that can be positioned freely or their moving path can be fixedly in the interior space of the mixing tank, wherein the mixing aids can comprise at least one of bearing balls ranging in number from 1 to 20 and more preferably 2 to 15. The mixing tank volume can range from 10 mL to 100 L, preferably from 20 mL to 80 L, more preferably from 50 mL to 60 L and the volume of water in the mixing tank can range from 9 mL to 99 L, preferably 19 mL to 79 L and more preferably 29 mL to 59 L.

FIG. 9 is a preferred method 900 embodiment of the current invention for generating and releasing a 1-MCP gas. In a step 910, establishing a mixture comprising a carrier complex in water within an interior space of a mixing tank. In step 920 releasing a gaseous form of 1-MCP from the carrier complex by the application of a releasing force provided through the operational connection of the mixing tank to an electromagnetic element, such as an electromagnetic coil.

Figure 10:
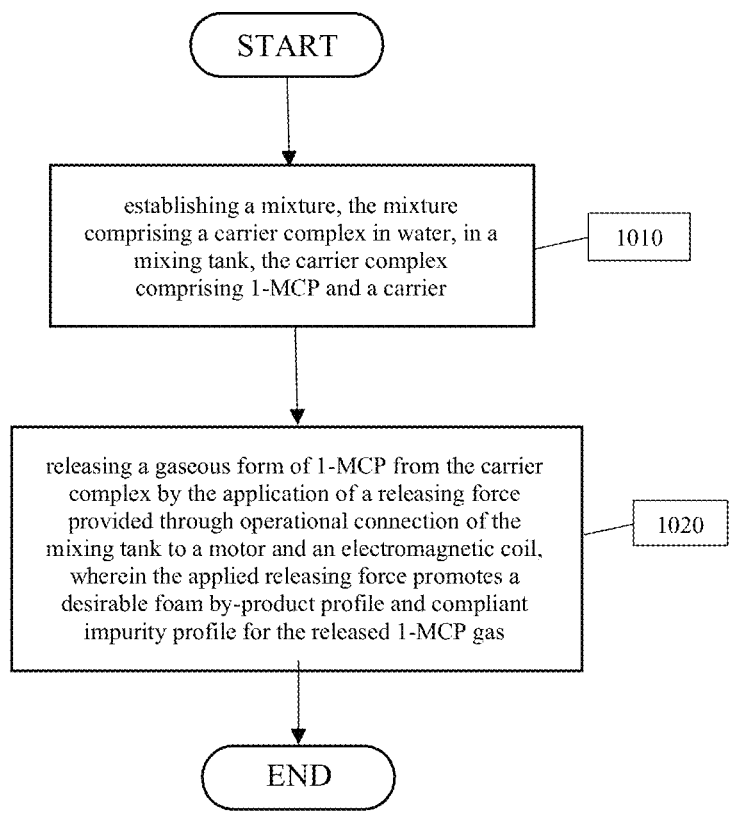
FIG. 10 is a block diagram illustrating a sixth preferred method for releasing a 1-MCP gas in accordance with an exemplary embodiment of the current invention.

FIG. 10 is a preferred method 1000 embodiment of the current invention for generating and releasing a 1-MCP gas. In a step 1010, establishing a mixture comprising a carrier complex in water within an interior space of a mixing tank. In step 1020 releasing a gaseous form of 1-MCP from the carrier complex by the application of a first releasing force and a second releasing force in concurrent application. The first and second releasing forces can be provided through the operational connection of the mixing tank to a motor and an electromagnetic element, such as an electromagnetic coil. The motor and/or electromagnetic element can apply either of the first and/or second releasing forces of method 1000.

For the exemplary method embodiments, including FIGS. 9 & 10, the process of releasing 1-MCP gas can further promote and/or provide a desirable foam by-product profile by promoting the reduction and/or avoidance of foam by-product generation and can promote formation of a compliant impurity profile for the released 1-MCP gas in accordance with the current invention. As described above herein, the method embodiments can promote greater than 96%, more preferably 100%, of 1-MCP gas being released from the carrier complex. The amount of carrier complex can range from 0.001 kg to 10 kg, preferably 0.01 kg to 6 kg and more preferably 0.02 kg to 1 kg and the ratio of carrier complex to water ranges from 1:500 to 1:5 and more preferably 1:100 to 1:10. The carrier complex can be placed directly into the water in the interior space of the mixing tank or, at least initially, indirectly placed into contact with the water in the mixing tank by being contained in at least one of a water permeable material, water soluble and/or dissolvable polyvinyl alcohol pouch, water soluble and/or dissolvable paper bag and various other water soluble and/or dissolvable containers, films or pouches as may be contemplated. The carrier that can be complexed with 1-MCP to form the carrier complex can comprise one or more of an encapsulant(s) and/or adsorbent(s), preferably α-cyclodextrin, metal organic framework, zeolites, activated carbons, cucurbit[6]uril, and other polymeric or porous materials such as gelatin and pectin.

The generator employed with the method embodiments can provide one or more device(s) and/or mechanism(s) which can apply the one or more releasing force(s), such as the first and second releasing forces of method 1000, during an operation time to the mixture in the mixing tank. The releasing force(s), as described, may comprise at least one of a rotational, stirring, shaking and/or vibratory (oscillatory) force, in at least one of a continuous or intermittent manner. The application of the releasing force can also be promoted with the mixing tank tilted at an angle relative to a planar surface, such as the holding plate as described in FIG. 2. The motor and/or electromagnetic element, such as an electromagnetic coil or other similar device or mechanism as contemplated by those skilled in the art, can be powered by direct current or alternating current.

The electromagnetic coil can generate the stirring of a magnetic stir bar with rpm ranges from 15-50000 rpm, preferably 15-30000 rpm, more preferably 15-20000 rpm. The magnetic stir bar being positioned to interact with the mixture. Thus, for any of the exemplary embodiments employing a magnetic stir bar in operational connection with an electromagnetic element, it can be understood that the magnetic stir bar is or can be positioned within the mixing tank within which the mixture is contained. The operation time can range from 5 minutes to 48 hours, preferably from 5 hours to 30 hours, more preferably from 10 hours to 24 hours. The operation can be continuous or intermittent. In the case of intermittent rotation, the total time of mixing/agitation can range from 5 minutes to 48 hours, preferably from 5 hours to 30 hours, and more preferably from 10 hours to 24 hours. The stir bar can rotate around a fixed axis or around a fixed point. Stirring around a fixed point can promote larger surface area covered by stirring. The surface area is dependent on the length of the stir bar, the volume of the water, and the size of the mixing tank. The covered stirring surface area can range from 10% to 100%, or 50%-100% of the surface area of the mixing tank. The stirring can be continuous or intermittent. The operation time can range from 5 minutes to 48 hours, preferably from 5 hours to 30 hours, more preferably from 10 hours to 24 hours. The intermittent rotation can be controlled by a control system such as a programmable relay cycle timer. The intermittent operation can be more cost and energy-effective than continuous operation, and can sustain longer treatment time.

As described, the mixing tank and/or mixture can have one or more releasing forces being applied to it, via operational connection with a motor or other mechanism(s) as contemplated, and such additional releasing force(s) can be one or more of two and three dimensional applications. For instance, a rotational releasing force can be applied to a mixing tank, through operational connection with a motor, in addition to the stirring force. The speed of rotation imparted to the mixing tank can be at least one of 15-50000 rpm, preferably 15-30000 rpm and more preferably 15-20000 rpm. It is further contemplated that alternative stirring mechanisms, such as a stirring mechanism comprising a stirring rod with propellers, preferably 1 to 10, more preferably 1 to 4 and/or a magnetic stir bar with stirring speed of 15-50000 rpm, preferably 15-30000 rpm and more preferably 15-20000 rpm, can be employed. It is also contemplated that such a stirring mechanism may be operationally connected with the motor. Where a gyratory movement is desired to be generated, the mixing tank can be established at a tilt angle relative to a horizontal planar surface. The tilt-angle relative to the planar surface can range from 5°-60°, preferably 5°-50° and more preferably 5°-30°. The 1-MCP generator employed for accomplishing the method 500 can provide a tortious (torque) force ranges from 0.0001 to 300 Nm, preferably 0.0002 to 100 Nm, more preferably 0.0002 to 50 N·m. It is also contemplated that the operation time can range from 5 minutes to 48 hours, preferably from 5 hours to 30 hours, more preferably from 10 hours to 24 hours. The exemplary method(s) may also employ the use of one or more mixing aids that can be positioned freely or their moving path can be fixedly established in the interior space of the mixing tank, wherein the mixing aids can comprise at least one of bearing balls ranging in number from 1 to 20 and more preferably 2 to 15. The mixing tank volume can range from 10 mL to 100 L, preferably from 20 mL to 80 L, more preferably from 50 mL to 60 L and the volume of water in the mixing tank can range from 9 mL to 99 L, preferably 19 mL to 79 L and more preferably 29 mL to 59 L.

Preferred exemplary embodiments of the current invention can provide a mechanism to solubilize 100% 1-MCP complex in solvent and release 1-MCP quickly and efficiently. The current invention aims to achieve this by promoting control over the temperature of the mixing solution (a.k.a., mixture) in the generator, thereby, providing a temperature controlled mixture. Thus, the current invention employs a temperature control system for controlling the temperature of the mixture relative to a temperature of a surrounding environment.

The temperature control system can promote and/or provide a difference in temperature between the mixture and the surrounding environment ranging from 0-100° C. The temperature control system, during the 1-MCP release process, can promote and/or provide for the mixing solution to be established and/or maintained in the range of 1-100° C., preferably 10-80° C. and more preferably 10-60° C. The temperature control system, during the 1-MCP release process, can promote and provide the establishment and maintenance of the mixture at any of the indicated temperature ranges herein for various periods of time prior to, during and/or post—the 1-MCP release process, such periods of time may range from ten (10) minutes to 48 hours in the mixing tank, preferably twenty (20) minutes to 24 hours and more preferably at least thirty (30) minutes (0.5 hours) in the mixing tank. It is understood that the establishment and/or maintenance of a temperature or temperature range can be provided during various time periods such as when the mixture is in the generator including, without limitation, the mixing tank, and for at least some period of time prior to or post the 1-MCP release process and at least some portion of the 1-MCP release process.

A surrounding environment is any environment that is outside of the environment provided for the mixture by the generator, such as when the mixture is established and maintained within the mixing tank, of the current invention. Thus, a surrounding environment can be any controlled environment, such as within a room, treatment room and/or control room (as described herein) or any uncontrolled environment, such as any outdoor or other ambient environment. The mixing tank and/or generator of the current invention can be established individually or as part of a system in various environments and provide its novel 1-MCP release process. For example, a generator of the current invention can be established within a treatment room environment for respiring produce, wherein the treatment room provides and maintains an environment with at least a temperature range of −20° C. to 100° C. and preferably at least a temperature of −1° C. The generator including the temperature control system of the current invention can be employed within such a treatment room environment and provide the unique capabilities including, without limitation, the temperature range and time range controls for various periods of time during the 1-MCP release process. As shown and described throughout the instant application, the generator can promote and provide for the establishment and/or maintenance of the mixture at a certain temperature and/or range of temperature during at least some portion of the 1-MCP release process. The processes, methods and system(s) capabilities can be promoted and provided by the current invention when the generator is established within any controlled environment, including within a treatment room as described above and/or in an outside (ambient) environment, such that the mixture can be established and/or maintained within the various temperature ranges and periods of time, or at specified temperature(s) or time(s), during at least some portion of the 1-MCP release process as is described herein.

The temperature control enabled by the current invention can include, without limitation, a promoted modification and/or maintenance of the temperature of the mixture in the generator. Modification can include a promoted establishment of a decrease or increase in a temperature of the mixture in the generator as from a starting or initial mixture temperature. A starting mixture temperature can be an initial temperature established and/or promoted for the mixture by the current invention or an initial temperature found for the mixture. The initial temperature for a mixture can be established as an ambient environment temperature or through the addition of one or more various temperature control sources such as, without limitation, by adding hot and/or cool water. The temperature of the water, or one or more alternative sources, added may range from 0-100° C. The starting mixture temperature can range from 0-100° C. or such other starting temperature as may be contemplated and used with the current invention. The temperature control promoted by the current invention can be variously provided and implemented including, but not limited to, by enabling a heating (and cooling) of the mixing solution and insulating the mixing tank of the generator using insulation materials.

In exemplary contemplated aspects consistent with embodiments of the current invention, a 1-MCP generator can have a temperature control system that may comprise any individual device(s), mechanism(s), and technology(ies) or a combination of systems and technologies. By way of example(s), the system(s) can include, without limitation, an (i) insulation system (aka, insulator) and (ii) heating system. The contemplated system(s) and technologies can be employed to promote the establishment and maintenance of a temperature or temperature range for a mixing solution in a generator.

An exemplary temperature control system can employ various component(s) features with (i) insulation to promote the establishment and/or maintenance of a desired temperature of the mixing solution or (ii) a heater system to promote the establishment and/or maintenance of a desired temperature of the mixing solution. It is further contemplated that the various component features, such as those that may be found for the insulation and heater systems, can be employed individually or in combination to provide the temperature control capabilities desired.

An insulation system can include and comprise various insulation materials that can be employed with the current invention. It is contemplated that various commercially available insulation devices and mechanism can be employed with the current invention such as, without limitation, SmartPak™ (SmartPak Equine LLC) insulating materials and others as may be contemplated and available. Various contemplated materials may include, but are not necessarily limited to, fiberglass, mineral wool, cellulose, natural fibers, polystyrene, polyisocyanurate, polyurethane, vermiculite and perlite, urea-formaldehyde foam, cementitious foam, phenolic foam, and air. The insulation materials employed may have various insulation ratings, characteristics and/or various other indicators of its insulation providing properties as are known in the field. The insulation materials may be employed individually or in various combinations without departing from the scope and spirit of the current invention.

The insulation materials can have various configurations and can be implemented in direct and in-direct contact with the generator, mixing tank and/or mixing solution. The insulation materials can be used to cover 5-100%, preferably 50-90% of the surface area of the generator and/or mixing tank. The thickness of the insulation material can range from 0.001-1 meter, preferably 0.002-1 meter, more preferably 0.005-1 meter.

It is contemplated that the heating system, in at least one embodiment of the current invention, can comprise at least one heating element which may be used to promote the application of an amount of heat to the mixing solution. The heating element can have a power level of 1-15000 Watt, preferably 10-10000 Watt, more preferably 10-6000 Watt. The heating element can be submerged, partially or fully, in the mixing solution or placed in the headspace of the mixing tank. It can be powered using direct current or alternate current. It is contemplated that other means, as are known in the art, for applying an amount of heat, whether to the generator, mixing tank and/or mixture, for the current invention may be employed and the configuration and implementation of such may vary as has been described and may be contemplated.

Various additional capabilities may be enabled by and for the contemplated temperature control system of the current invention. For example, a temperature control sensor can be incorporated into the system to promote the identification and maintenance of a desired temperature or temperature range for the mixing solution. The sensor may promote the avoidance of over-heating of the mixture (i.e., releasing solution) and damage to the mixing tank and/or generator. It is further contemplated that a cooling capability can be provided by the temperature control system of the current invention. This may be enabled using various different cooling technologies and various direct and/or indirect application to the generator, mixing tank and/or mixture as may be contemplated by those skilled in the art.

The temperature control system, whether employing, individually or in combination, insulation and/or a heating system(s) can be used to promote the controlled release 1-MCP gas from the mixture in the generator. For instance, a generator of any of the various embodiments for the current invention, and specifically those employing the temperature control system herein described, may achieve the release of 1-MCP gas from the mixture in less than 15 hours, preferably in less than 5 hours, more preferably in less than 3 hours. As has been described throughout, the percentage release of the 1-MCP gas promoted may achieve a 100% or substantially 100% release. This percentage release being promoted in accordance with the timelines described herein.

Relative to the temperature of a surrounding environment, it is contemplated that the generator can be designed to promote the mixing solution at a higher temperature to solubilize complex in a shorter time or can be designed to have the mixing solution at lower temperature with good insulation to provide the equivalent result. It is contemplated that a generator including the temperature control system described herein, may be established in a surrounding environment that is colder or hotter than the optimal temperature for a mixture and the achievement of the desired percentage of 1-MCP gas release from that mixture. For instance, the generator may be physically established within an enclosed environment (e.g., room) that is held at a temperature of roughly thirty-two degrees Fahrenheit. It can be that the mixture in the generator requires a temperature of forty-eight degrees Fahrenheit for achieving the desired percentage release of 1-MCP gas. The temperature control system can provide a generator, whether through the use of insulation and/or heating system capabilities, alone or in combination, that can promote, without limitation, establishing and maintaining the mixture at the desired higher temperature, relative to the surrounding environment, for at least some period of time. That period of time generally being understood as the time needed for achieving the desired percentage release of 1-MCP gas from the mixture which may vary significantly as has been described herein throughout. Alternatively, the generator may be physically established in a surrounding environment with a higher temperature than optimal for achieving the desired percentage release of 1-MCP gas from the mixture. Thus, a generator of the current invention may be enabled to establish and maintain the mixture at a desired temperature that is lower than that surrounding the generator, again, for at least some period of time.

Other factors may impact upon the mixture temperature requirements to be met and maintained by the current invention. For instance, the amount of complex in the mixture can be adjusted in any given scenarios to generate the desired percentage release results. Thus, it is contemplated that those of ordinary skill in the art can select a range of temperature and/or a combination of water temperature, ratio of 1-MCP complex to water, and insulation to obtain the desired results as has been described herein for the various embodiments of the current invention.

In an exemplary embodiment, a 1-MCP generator can comprise a mixing tank operationally connected with an agitation system and a temperature control system. As described herein throughout, the mixing tank can comprise an integrated tank unit or may be comprised of and include various individual, separate component features such as a container (aka, receptacle) and a lid that can operationally connect with together. The component features can be of various dimensional and operational configurations and provide a receptacle into which various materials employed for the current invention may be placed and operationally engaged with. For example, the receptacle may be generally configured as a five gallon container (e.g., a bucket) that includes an integrated or can connect with a lid. Alternatively, receptacles of various sizes capable of receiving and containing various volumes of different materials can be employed, such as a receptacle that may hold volumes ranging from ounce(s) to hundreds of gallons, milliliters to hundreds of liters, or such other volumes as may be contemplated. The lid can be configured as integrated or to connect with the receptacle in any manner, utilizing various different connecting technologies, as may be contemplated by those skilled in the art. The lid may provide or cover in whole or in part the container component. The lid may include a stirring connection mechanism, wherein this mechanism includes various additional components and/or features that enable the connection with the agitation system. The connection of the agitation system with the lid may be enabled utilizing various connection technologies as contemplated. It is further contemplated that the agitation system may be fully or partially integrated with the lid in various manners. The lid, whether integrally formed with or connected to the agitation system, enables the operation of the agitation system with the 1-MCP generator as described herein.

In an exemplary, contemplated embodiment, a temperature control system for a 1-MCP generator includes a temperature control system operationally connected with a 5-gallon container configured and enabled to operationally connect both with a lid and agitation system. The temperature control system comprises an insulation system that is configured to provide and promote a desired insulation effect for the generator regardless of the physical location of the generator and the surrounding or ambient environment. In exemplary embodiments, the insulation system can be understood as a sleeve system. It is contemplated that the insulation system may be configured and enabled in various manners as desired by those skilled in the art. A sleeve system includes one or more component forms (sleeve form) that are configured and capable of operationally connecting, directly or indirectly, individually or in combination, with the integrated or one or more individual components (outside the sleeve itself) of the 1-MCP generator. By way of example, without limitation, a sleeve system may provide a first sleeve form that is configured to be placed in connection with the mixing tank. It is contemplated that this first sleeve form configuration enables the mixing tank to be at least partially or fully encompassed within and surrounded by it. Where the mixing tank is configured as a 5-gallon bucket (container) with a lid that is removably connectable, thereby, capable of establishing an open top end of the container when the lid is removed. The first sleeve form can be understood as configured to allow the container to be inserted within, surrounding or encompassing the full exterior surface of the container and leaving the open top end of the container available for connection with the lid or any other device contemplated. Thus, the first sleeve form can be understood to have an open end into which the container may be inserted and allowing for the top to remain open. It is contemplated that the first sleeve form may be integrally formed or removably connected with a sleeve top or sleeve lid, which may be referred to as a second sleeve form, that allows and enables the functional capabilities required for using the form with a particular container form. The sleeve top or sleeve lid may be enabled to be partially disconnected or removed from its connection with the rest of the sleeve form. It is contemplated that, for instance, a zipper, loop and hook fastener(s) or other fasteners may be employed that enable the sleeve top or sleeve lid operational connection with the rest of the sleeve form. It is further contemplated that the insulation system be configured with multiple components, thus, for the example being described, the insulation system may comprise at least a first and second sleeve form. In this example, the second sleeve form is separate from but operationally may be connected with the first sleeve form and can be understood as configured to surround or encompass, partially or fully, the lid of the container of the generator.

Where it is desirable to have a section or more than one section of the lid accessible, for various purposes such as, without limitation, connecting of the agitation system, placement of various items within the interior of the container, and such other purposes as may be contemplated, the second sleeve form can be configured in any manner that promotes the accomplishing of the required desired purpose(s) while providing as substantial of coverage as possible and promoting the maximum insulation of the lid. Any sleeve form may include various other designs, labels and configurations to achieve a desired purpose and provide the insulation effect to a generator. and enabled in component sleeve forms. Still further, a sleeve form may include a flap, fold over or other section that can be at least partial disconnected and then reconnected to the sleeve form. In this manner, the flap, fold over or other section may be of a smaller dimensional configuration than the rest of the sleeve form. The design of the sleeve and any other feature of a sleeve may be based on contemplated characteristics and/or requirements presented by features of a 1-MCP generator of the current invention.

The agitation system, as has been described throughout the instant specification, can be variously configured as a stirring, mixing and other types of mechanisms. It is contemplated that the agitation system operationally connects with the 1-MCP generator via the lid or container or the integrated tank unit. These various mechanisms operationally engage with and can provide for an agitation of the components that may be found in the mixing tank. For example, a stirring mechanism may be employed wherein a stirring rod is connected with a stirring device and a motor. As described herein, the motor connects with one end of the stirring rod and can impart a rotational force to the stirring rod that causes it to rotate at speed. The size of the motor and rotational force it can impart to the stirring rod may vary as described for the various embodiments herein. The speed or number of revolutions per minute (rpm) with which the stirring rod is rotated can vary significantly as described herein. Connected at an end of the stirring rod opposite from the connection of the motor is the stirring device. The stirring device can be variously configured as has been described for the various embodiments herein. For example, the stirring device may include an adapter mechanism that can connect to the stirring rod and then is also connected with one or more stirring arms. The adapter mechanism may be variously configured in its dimensions and shape. Further, the adapter mechanism may include various features and components that enable its functional capabilities. For instance, the connection with the stirring rod and one or more of the stirring arms may enable it to connect and release from the stirring rod and allow the one or more stirring arms to connect and release from the adapter mechanism. Various different connecting technologies may be employed with and for the current invention as for the adapter mechanism, the stirring rod, the motor and any other component feature(s) of the exemplary and contemplated embodiments of the current invention. The stirring arms may be configured in various dimensions and shapes and may be similarly or differently configured from one another. The connection of the stirring arms with the adapter mechanism may also enable one or more of the arms to be retracted, folded or otherwise repositioned. The connection of the stirring arms may include a locking mechanism that enables the positioning of the stirring arms to be temporarily or permanently fixed in one or more locations.

Figure 11:
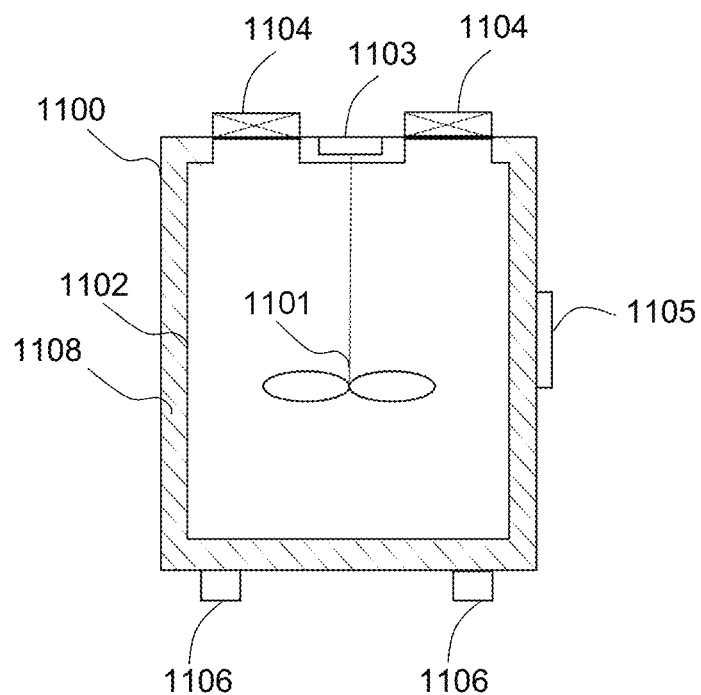
FIG. 11 is an illustration of an insulated stirring generator in accordance of the current invention.

A preferred embodiment of a 1-MCP generator 1100 is shown in FIG. 11. It is contemplated that numerous and various preferred embodiments for the current invention can utilizing the 1-MCP generator 1100 shown in FIG. 11. This embodiment provides a stirring 1-MCP generator 1100 further comprising an exemplary temperature control system, for this embodiment that is a polyurethane insulation layer 1108, which covers a mixing tank 1102. Insulation materials include but not limited to fiberglass, mineral wool, cellulose, natural fibers, polystyrene, polyisocyanurate, polyurethane, vermiculite and perlite, urea-formaldehyde foam, cementitious foam, phenolic foam, and air. These insulation materials can have various configurations and can be with direct and in-direct contact with the mixing solution. The insulation materials can cover 5-100%, preferably 50-90% of the surface area of the mixing tank. The thickness of the insulation material can range from 0.001-1 meter, preferably 0.005-0.1 meter. The total volume of mixing tank 1102 can be anywhere between 10 mL to 100 L, preferably 20 mL to 80 L, more preferably 50 mL to 60 L; two ventilation fans 1104, a mechanical motor 1103 attached on the lid of the generator, a stirring rod with propeller 1101 attached on the motor, two wheels 1106, and a control panel 1105 that controls the on and off of the generator, and operation time of the ventilation fan. The motor has a rotation speed of 15-50000 rpm, preferably 15-30000 rpm, more preferably 15-20000 rpm. The mixing tank can contain water of 9 mL to 99 L, preferably 19 mL to 79 L, more preferably 29 mL to 69 L. The temperature of the water (mixing solution) can be maintained for various time periods including, without limitation, for at least portion of the 1-MCP Release Process, preferably in the range of 1-100° C., more preferably in the range of 10-80° C., most preferably in the range of 10-60° C.

Figure 12:
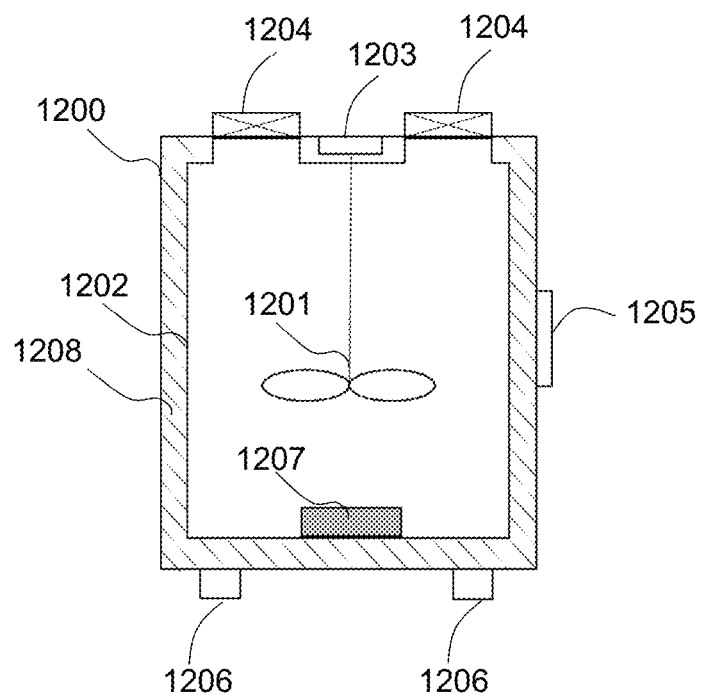
FIG. 12 is an illustration of an insulated and heated stirring generator in accordance with the current invention.

A preferred embodiment of a 1-MCP generator 1200 is shown in FIG. 12. It is contemplated that preferred method and system embodiments for the current invention can be accomplished utilizing the 1-MCP generator 1200 shown in FIG. 12. This embodiment provides a stirring 1-MCP generator 1200 comprising a polyurethane insulation layer 1208 covering a mixing tank 1202, with total volume of 10 mL to 100 L, preferably 20 mL to 80 L, more preferably 50 mL to 60 L; two ventilation fans 1204, a mechanical motor 1203 attached on the lid of the generator, a stirring rod with propeller 1201 attached on the motor, a submersion water heater 1207 attached on the bottom of the mixing tank, two wheels 1206, and a control panel 1205 that controls the on and off of the generator, and operation time of the ventilation fan. The motor has a rotation speed of 15-50000 rpm, preferably 15-30000 rpm, more preferably 15-20000 rpm. The mixing tank can contain water of 9 mL to 99 L, preferably 19 mL to 79 L, more preferably 29 mL to 59 L. The temperature of the water (mixing solution) can be maintained for various time periods including, without limitation, for at least portion of the 1-MCP Release Process, preferably in the range of 1-100° C., more preferably in the range of 10-80° C., most preferably in the range of 10-60° C.

The heating element 1207 can have a power level of 1-15000 Watt, preferably 10-10000 Watt, more preferably 10-6000 Watt. It can be submerged in the mixing solution or placed in the headspace of the mixing tank. It can be powered using direct current or alternate current. A temperature control sensor can be incorporated into the heater to maintain the temperature of the mixing solution at certain level to avoid over-heating of the releasing solution and damage to the mixing tank. Insulation layer and/or heater can be used as temperature control systems, either individually or in combination, to release 1-MCP anywhere within 10 min to 10 hours, preferably within 15 min to 5 hours, more preferably within 30 min to 3 hours. The generator can be designed to have the mixing solution at higher temperature to solubilize complex in a shorter time without insulation or can be designed to have the mixing solution at lower temperature with good insulation to provide the equivalent result. Further the amount of complex can be adjusted in each such scenarios to generate similar results. People with ordinary skill related to the art can simply design different combinations of temperature, amount of 1-MCP complex and insulation to obtain the desired results.

The abovementioned specifications and properties for generators with insulation or using water with specific temperature could also be used for applications which do not have any temperature control by people with ordinary skill in the art. Such specifications and properties include motor rotation speed, tank volume, and water volume. These specifications and properties can increase the capacity of the treatment and shortens the treatment time.

In one embodiment of the current invention, a connection between the generator and the treatment area can be provided so that the generator can be placed outside of the treatment area and 1-MCP can be transferred into the treatment area from the generator through the connection. Placing the generator outside of the treatment area can provide multiple benefits including but not limited to avoidance of the interference to other treatments such as controlled atmosphere, convenience of monitoring the operation of the generator, and convenience of gas sample collection to monitor the release of 1-MCP. The connection can be achieved using a flexible or rigid pipe that connects the generator and the opening on the treatment area. The pipe can be made using materials such as nylon, aluminum, high density polyethylene, and other materials that do not absorb or react with 1-MCP. Rubber gaskets or other sealant materials are needed at the connecting points to ensure air tightness. The length of the pipe can range from 0.1 to 100 meters, preferably 0.1 to 50 meters, more preferably from 0.1 to 10 meters. The diameter of the pipe can range from 0.001 to 2 meters, preferably 0.001 to 1 meter, more preferably 0.001 to 0.1 meter. Adaptors can be used to help connect the pipe to the opening on the door of the treatment area to ensure air tightness.

To facilitate the gas transfer from the generator to the treatment area through the pipe, improved air circulation in the generator headspace and/or pressure difference between the generator headspace and storage room are needed, which can be achieved using multiple approaches including but not limited to (1) pumping air or other inert gases into the generator headspace or releasing mixture to create possible pressure in the generator to push 1-MCP into the pipe and treatment area, (2) circulating the headspace using a fan to create air current to push 1-MCP into the pipe and treatment area, and (3) withdrawing the gas in the headspace of the generator and pumping the gas into the treatment area. The first approach can be achieved using a gas pumping mechanism which includes but not limited to equipment such as air compressors, portable gas tanks, and air pumps. These equipments can deliver gas pressure ranging 0-250 psi, preferably 2-200 psi, more preferably 2-150 psi. The gas flow rate can be further controlled using a gas regulator and the flow rate can range 0.001-200 L/min, preferably 0.01-200 L/min, more preferably 0.01-180 L/min. The gas or gas mixtures can include but not limited to air, nitrogen, argon, and gas mixtures that are used to create the controlled atmosphere in the treatment area. They can be fixed on the generator or connected to the generator using a tube or pipe which can extend further to the releasing mixture. The second approach can be achieved using a fan operating at speed ranging 10-5500 rpm, preferably 50-3500 rpm. The third approach can be achieved using an air pump to create an air flow rate ranging 0.001-200 L/min, preferably 0.01-200 L/min, more preferably 0.01-180 L/min. The operation of the air pumping mechanism and the fan can be continuous or intermittent, and powered by direct or alternating current. To prevent gas back flow, one-way check valves can be installed on the pipe or tube. Flow meter and/or pressure gauges can be installed on the generator to monitor the flow rate and pressure to ensure the operation of the generator. Safety valves can be installed on the generator to avoid excessive pressure buildup in the generator headspace. Leak detectors can be used to ensure air tightness and complete transfer of the generated 1-MCP into storage room.

Figure 13:
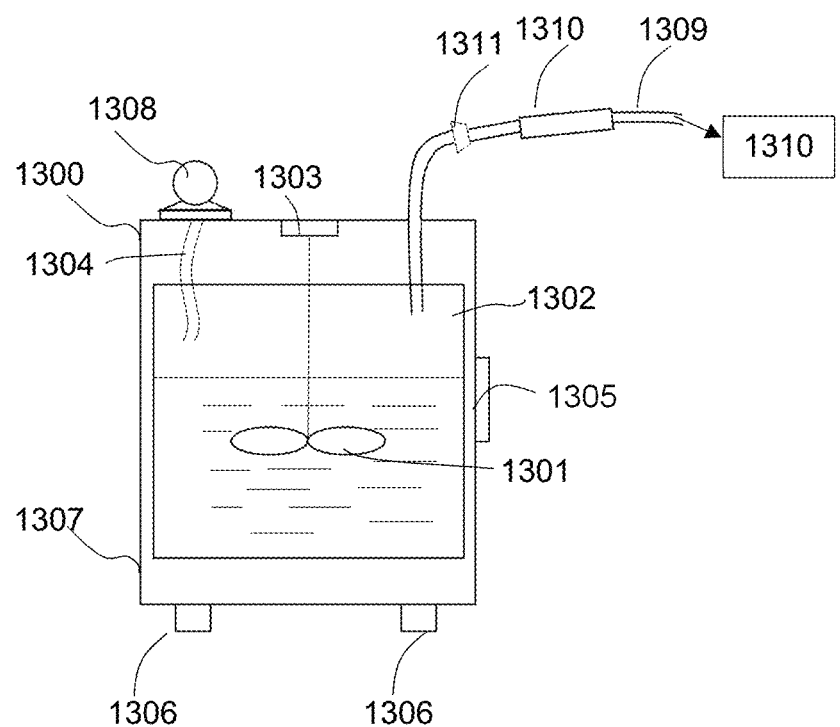
FIG. 13 is an illustration of a stirring generator that can be placed outside of the treatment area using an air pump to push air into the generator headspace in accordance with the current invention.

A preferred embodiment of a 1-MCP generator 1300 is shown in FIG. 13. It is contemplated that preferred method and system embodiments for the current invention can be accomplished utilizing the 1-MCP generator 1300 outside of the storage facility. This embodiment provides a stirring 1-MCP generator 1300 comprising a receptacle 1307 configured to removably connect with a removable mixing tank 1302, with total volume of 10 mL to 100 L, preferably 20 mL to 80 L, more preferably 50 mL to 60 L; a portable air pump 1308 placed on the top of the lid, one tube 1304 connected to the air pump and goes through the lid to the headspace of the generator, one pipe 1309 that connects the generator to the treatment room containing the produce (secondary location) 1310, one mechanical motor 1303 attached on the lid of the generator, a stirring rod with submerging propeller 1301 attached on the motor, two wheels 1306, a control panel 1305 that controls the on and off of the generator, a check valve 1311, and a flow meter 1310. The motor has a rotation speed of 15-50000 rpm, preferably 15-30000 rpm, more preferably 15-20000 rpm. The mixing tank contains water of 9 mL to 99 L, preferably 19 mL to 79 L, more preferably 29 mL to 59 L. The temperature of the water (mixing solution) is maintained for at least portion of the 1-MCP Release Process, preferably in the range of 1-100° C., more preferably in the range of 10-80° C., most preferably in the range of 10-60° C. The air pump delivers air at flow rate of 0.001-200 L/min, preferably 0.01-200 L/min, more preferably 0.01-180 L/min. People with ordinary skill and art in the field can select the flow rate of the air pump based on the release rate of 1-MCP and volume of the headspace in the generator.

Figure 14:
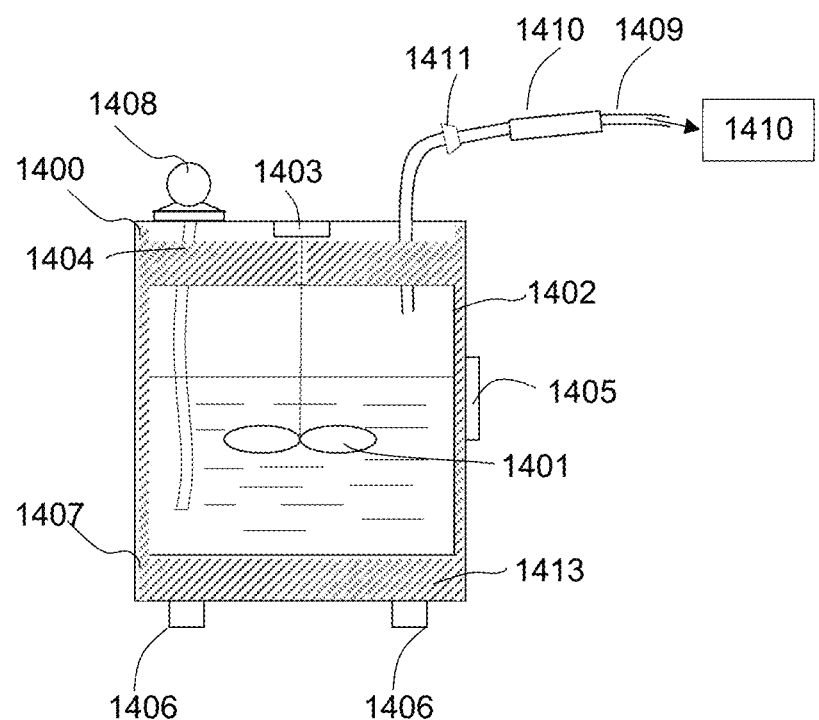
FIG. 14 is an illustration of an insulated stirring generator that can be placed outside of the treatment area using an air pump to push air into the mixing solution in accordance with the current invention.

A preferred embodiment of a 1-MCP generator 1400 is shown in FIG. 14. It is contemplated that preferred method and system embodiments for the current invention can be accomplished utilizing the 1-MCP generator 1400 outside of the storage facility. This embodiment provides a stirring 1-MCP generator 1400 comprising a receptacle 1407 configured to removably connect with a removable mixing tank 1402, with total volume of 10 mL to 100 L, preferably 20 mL to 80 L, more preferably 50 mL to 60 L; a portable air pump 1408 placed on the top of the lid, one tube 1404 connected to the air pump and goes through the lid to the releasing mixture in the generator, one pipe 1409 that connects the generator to the treatment room containing the produce (secondary location) 1410, one mechanical motor 1403 attached on the lid of the generator, a stirring rod with submerging propeller 1401 attached on the motor, two wheels 1406, a control panel 1405 that controls the on and off of the generator, a check valve 1411, and a flow meter 1410. The motor has a rotation speed of 15-50000 rpm, preferably 15-30000 rpm, more preferably 15-20000 rpm. The mixing tank contains water of 9 mL to 99 L, preferably 19 mL to 79 L, more preferably 29 mL to 59 L. The temperature of the water (mixing solution) is maintained for at least portion of the 1-MCP Release Process, preferably in the range of 1-100° C., more preferably in the range of 10-80° C., most preferably in the range of 10-60° C. The air pump delivers air at flow rate of 0.001-200 L/min, preferably 0.01-200 L/min, more preferably 0.01-180 L/min. The generator is also equipped with a polyurethane foam insulation layer 1413. People with ordinary skill and art in the field can select the flow rate of the air pump based on the release rate of 1-MCP and volume of the headspace in the generator.

Figure 15:
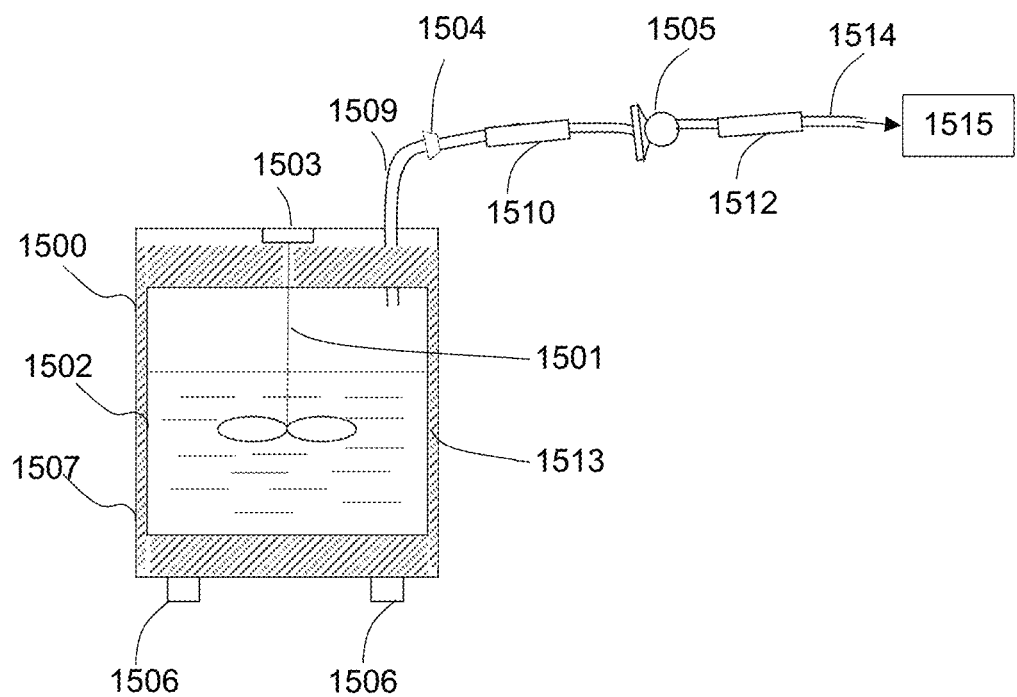
FIG. 15 is an illustration of an insulated stirring generator that can be placed outside of the treatment area using a vacuum pump for gas transfer in accordance with the current invention.

A preferred embodiment of a 1-MCP generator 1500 is shown in FIG. 15. It is contemplated that preferred method and system embodiments for the current invention can be accomplished utilizing the 1-MCP generator 1500 outside of the storage facility. This embodiment provides a stirring 1-MCP generator 1500 comprising a receptacle 1507 configured to removably connect with a removable mixing tank 1502, with total volume of 10 mL to 100 L, preferably 20 mL to 80 L, more preferably 50 mL to 60 L. A mechanical motor 1503 is attached onto the lid of the generator and is connected to a stirring rod with submerging propeller 1501. The whole set-up 1500 is on wheels 1506 for mobility of the system. An outlet pipe 1509 exits from mixing tank 1502. The outlet pipe 1509 is followed by one way check valve 1504 to prevent gas backflow. An air pump 1505 is attached between two flow meters 1520 and 1512 to push the gas into the treatment room containing produce (secondary location) 1515 through a connection fitting 1514.

The motor has a rotation speed of 15-50000 rpm, preferably 15-30000 rpm, more preferably 15-20000 rpm. The mixing tank contains water of 9 mL to 99 L, preferably 19 mL to 79 L, more preferably 29 mL to 59 L. The temperature of the water (mixing solution) can be maintained for various time periods including, without limitation, for at least portion of the 1-MCP Release Process, preferably in the range of 1-100° C., more preferably in the range of 10-80° C., most preferably in the range of 10-60° C. People with ordinary skill and art in the field can employ other methods of mixing MCP-cyclodextrin complex and water solution such as submersible pump, etc. to achieve a similar or substantially similar result as disclosed in this invention.

The air pump delivers air at flow rate of 0.001-200 L/min, preferably 0.01-200 L/min, more preferably 0.01-180 L/min. The generator is also equipped with a polyurethane foam insulation layer 1513 to maintain the temperature of the releasing solution. People with ordinary skill and art in the field can select the flow rate of the air pump based on the release rate of 1-MCP and volume of the headspace in the generator.

Figure 16:
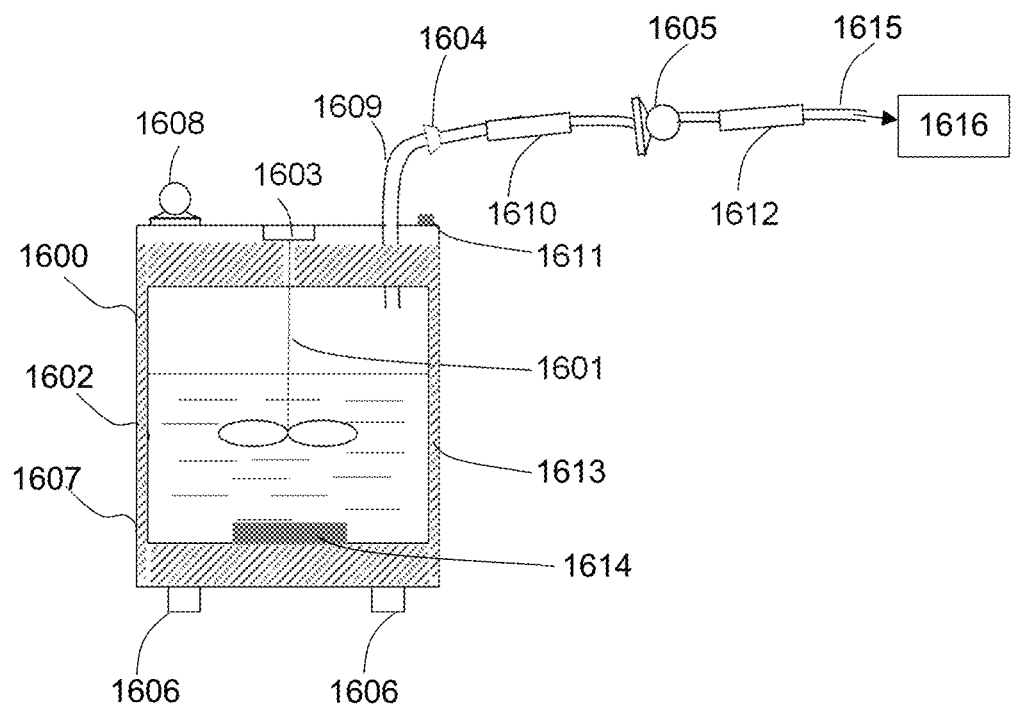
FIG. 16 is an illustration of an insulated and heated stirring generator with heat element that can be placed outside of the treatment area using a vacuum pump for gas transfer in accordance with the current invention.

A preferred embodiment of a 1-MCP generator 1600 is shown in FIG. 16. It is contemplated that preferred method and system embodiments for the current invention can be accomplished utilizing the 1-MCP generator 1600 outside of the storage facility. This embodiment provides a stirring 1-MCP generator 1600 comprising a receptacle 1607 configured to removably connect with a removable mixing tank 1602, with total volume of 10 mL to 100 L, preferably 20 mL to 80 L, more preferably 50 mL to 60 L. A submersion water heater 1614 is placed inside the mixing tank 1602 to maintain the temperature of the releasing solution (water). A mechanical motor 1603 is attached onto the lid of the generator and is connected to a stirring rod with submerging propeller 1601. The whole set-up 1600 is on wheels 1606 for mobility of the system. The generator 1600 is equipped with a safety valve 1611 to avoid excessive pressure buildup. An outlet pipe 1609 exits from mixing tank 1602. The outlet pipe 1609 is followed by one way check valve 1604 to prevent gas backflow. An air pump 1605 is attached between two flow meters 1610 and 1612 to push the gas into the treatment room containing produce (secondary location as defined herein below) 1616 through a connection fitting 1615. The motor has a rotation speed of 15-50000 rpm, preferably 15-30000 rpm, more preferably 15-20000 rpm. The mixing tank contains water of 9 mL to 99 L, preferably 19 mL to 79 L, more preferably 29 mL to 59 L. The generator is also equipped with a foam insulation layer 1613 to maintain the temperature of the releasing solution (water). The temperature of the water (mixing solution) can be maintained for various time periods including, without limitation, for at least portion of the 1-MCP Release Process, preferably in the range of 1-100° C., more preferably in the range of 10-80° C., most preferably in the range of 10-60° C. People with ordinary skill and art in the field can employ other methods of mixing MCP-cyclodextrin complex and water solution such as submersible pump, etc. to achieve a similar or substantially similar result as disclosed in this invention. The air pump delivers air at flow rate of 0.001-200 L/min, preferably 0.01-200 L/min, more preferably 0.01-180 L/min. People with ordinary skill and art in the field can select the flow rate of the air pump based on the release rate of 1-MCP and volume of the headspace in the generator.

The abovementioned specifications and properties for generators used outside of the treatment area could also be used for in-door applications, i.e., generators are placed in the treatment area, by people with ordinary skill in the art. Such specifications and properties include motor rotation speed, tank volume, water volume, and usage of a pump to transfer the generated gas from the generator to the treatment area. The current invention contemplates the use of various and alternative design combinations of temperature, amount(s) and composition(s) of 1-MCP complex, heating capabilities and characteristics and insulation materials and characteristics that can promote the achievement of the desired results. These specifications and properties can increase the capacity of the treatment and shortens the treatment time.

The 1-MCP Generators shown in FIGS. 13-16 can be employed in performing all the above described methods and processes of the current invention. For example, these exemplary generators may be used in a method 2500 for generating and releasing a 1-MCP gas. In a step 2510 a 1-MCP generator is established in a physical location with a surrounding ambient environment. The surrounding ambient environment may have a temperature ranging from −1° C. to 30° C. In a step 2520, establishing a mixture comprising a carrier complex in water within an interior space of a mixing tank at a desired temperature. The desired temperature for the mixture can range from 0° C. to 100° C. Preferably, the mixture temperature can be established for various time periods including, without limitation, for at least portion of the 1-MCP Release Process, in the range of 10° C. to 80° C., and more preferably in the range of 10° C. to 60° C. In step 2530 releasing a gaseous form of 1-MCP from the carrier complex by maintaining the mixture temperature, without limitation, for at least portion of the 1-MCP Release Process, at a range of 10° C. to 60° C. and the application of a releasing force provided through connection of the mixing tank to a motor. This is followed by a step 2540 where the 1-MCP gas is then directed to another physical location for dissemination. The direction provided may be through the use of a blower, fan or other means whereby the gas can be transmitted from the generator to another distinct physical location (called as secondary location in this invention) for respiring produce treatment outside the generator.

In another exemplary embodiment, a method for generating and releasing a 1-MCP gas can include establishing a 1-MCP generator in a physical location with a surrounding ambient environment. The surrounding ambient environment may have a temperature ranging from −1° C. to 30° C. Then establishing a carrier complex comprising 1-MCP complexed with at least one carrier on a separator within a housing, wherein a water reservoir including water is in operational connection with the carrier complex on the separator and the water is prevented from having direct contact with the carrier complex. Generating steam by heating the water in the water reservoir to at least 100° C. The steam temperature can range from 90° C. to 500° C., preferably 95° C. to 400° C. and more preferably 100° C. to 350° C. Releasing a gaseous form of 1-MCP from the carrier complex by promoting the interaction of steam with the carrier complex, the steam provided by heating the water to vapor phase.

In a still further exemplary embodiment a method for generating and releasing a 1-MCP gas includes establishing a 1-MCP generator in a physical location with a surrounding ambient environment. The surrounding ambient environment may have a temperature ranging from −1° C. to 30° C. Then establishing a carrier complex comprising 1-MCP complexed with at least one carrier on a separator within a housing, wherein a water reservoir including water is in operational connection with the carrier complex on the separator and the water is prevented from having direct contact with the carrier complex. Generating steam by heating the water in the water reservoir to at least 100° C. The steam temperature can range from 90° C. to 500° C., preferably 95° C. to 400° C. and more preferably 100° C. to 350° C. Applying a releasing force to the separator mixing tank provided through connection of the separator mixing tank to a motor. Allowing interaction of steam with the carrier complex, wherein the applied releasing force and steam interaction promotes the dissociation of 1-MCP from the carrier in complex and release of 1-MCP in gas form. It is contemplated that the application of the releasing force and steam interaction can be significantly concurrent and/or in a sequential manner as may be contemplated without departing from the scope and spirit of the current invention.

Additional exemplary embodiments of the current invention can comprise a system(s) for releasing 1-MCP, wherein the system employs any one or combination of two or more of the exemplary or contemplated embodiments for the 1-MCP generator(s) and/or temperature controlled 1-MCP generator(s) as have been described throughout the instant specification. It is further contemplated that the exemplary system(s) herein may be established and enabled to provide for the transmission and delivery of a released 1-MCP gas from the generator to a desired location. It is further understood that the use of the term "operational connection" and/or "operationally connected" shall, without limitation, have the following meaning: a direct or indirect, physical or relational, connection and/or association between things pertaining to or promoting enablement for providing a designated form or structure and accomplishing or achieving one or more designated functions or results. A connection shall be understood herein as referring to any type and manner of connection enabled through the use of various devices, mechanisms and technologies.

In additional exemplary embodiments the current invention can comprise a system that may include a temperature controlled 1-MCP generator operationally connected, via a transmission system, with a secondary location. The secondary location can be established and referred to herein as a control room, treatment room, storage facility, controlled atmosphere room or respiring produce storage environment. The secondary location, for exemplary embodiments, may be understood as a temperature controlled and regulatory compliant storage facility. Within such an exemplary control room it is contemplated that respiring produce (aka., fresh foods) may be located. It can be generally understood that for the purpose of applying treatment to the produce. The applied treatment can be understood as the application of the released 1-MCP gas from generator. For avoidance of doubt, the secondary location or control room may be a refrigerated control room wherein temperature is maintained from −0.5° C. to 5° C. The secondary location or control room may be a controlled atmosphere control room wherein in addition to temperature of −0.5° C. to 5° C., the atmosphere conditions are also maintained generally in the range of 0.1 to 5% O2 and 0.0 to 3% CO2.

For clarity, respiring produce as used herein can, without limitation, mean and refer to fresh-cut or whole fruits, vegetables, flowers and/or any other respiring food products. These fresh foods can be packed in flexible packaging (e.g., film) and/or semi-rigid and rigid containers (e.g., trays and/or lids) and placed into target treatment rooms (aka., control rooms or storage facilities). By way of non-limiting example, once produce such as apples and pears are harvested, they are cooled to remove field heat, after which they are stored under refrigeration (−0.5° C. to 5° C.) or controlled atmospheric condition which in addition to refrigeration has well defined cultivar specific $O_2$ and $CO_2$ atmosphere to maintain quality during storage. In exemplary embodiments, a generator of the current invention can be placed within the control room and release the 1-MCP gas directly into the refrigerated control room. However, in controlled atmospheric control room which has less than 5% of O2 and higher levels of CO2 can be, at least potentially, toxic/lethal environments. Therefore, there is a need to develop a 1-MCP generator that can release 1-MCP gas outside the control atmosphere control room and then deliver the released 1-MCP gas directly into the control atmosphere control room.

In preferred embodiments, the control atmosphere control room promotes and allows for the establishment and maintenance of various atmospheric conditions such as 0.1 to 5% O2 and 0.0 to 3% CO2. These atmospheric conditions within the room environment can be, at least potentially, toxic/lethal and therefore, in control rooms that has controlled atmosphere of less than 5% O2 and/or greater than 3% CO2. This creates a problem for efficient placement and use of a generator of 1-MCP gas and the promoted effects provided by achieving desired temperatures. These restrictions and toxic features of the environment requires a transmission and/or delivery mechanism for the 1-MCP gas generated by the generator of the current invention. In such instances, the generator is and can be located outside the secondary location or controlled atmosphere control room and, therefore, promotes the avoidance of interaction with the potentially toxic/lethal controlled environment room. However, the benefits of the low temperature(s), which include acting effectively to promote a slowing of the physiological degradation of respiring produce and extend shelf life make it useful to find ways to promote more efficient use and interaction with such environments.

The 1-MCP generator includes a temperature control system that comprises a polyurethane insulation layer, which covers a mixing tank. A lid, removably connectable with mixing tank, is operationally connected with a ventilation system that comprises a first ventilation fan and second ventilation fan and an agitation system that, for this exemplary embodiment, can comprise a mechanical motor operationally connected with a stirring rod that is further connected with a stirrer (e.g., propeller). A control panel controls the on and off of the motor and operation time of the first and second ventilation fans. It is further contemplated that control panel controls the on an off of an air pump of transmission system.

The operational connection of the generator to the control room is provided by a transmission system designed to provide for transmission between the generator and the control room. Thus, this system promotes the operational advantage of having the generator physically located outside the secondary location wherein the atmospheric conditions may not be conducive for humans. The transmission system may employ various mechanisms, devices and/or technologies as may be contemplated by those skilled in the art. In the current embodiment, transmission system provides its functionality by employing a pipe tubing (referred to herein as "pipe") operationally connected with an air pump. The pipe, via its pipe wall, has the general configuration of an open-ended cylindrical tube. It is contemplated that any mechanisms, devices and technologies, provided in various contemplated configurations, having various characteristics, and using various materials for providing the desired transmission capability may be employed to provide the transmission capabilities as shown herein by pipe.

Generator can be connected by, with or to a first end of pipe. A second end of pipe can be connected by, with or to the control room. In the current embodiment, the connection is made by employing a threaded, male and female, connector mechanism. It is contemplated that various different connection technologies, mechanisms, devices and systems may be employed with the current invention. First end shall define a first opening in operational connection with an interior passage. Second end shall define a second opening in operational connection with the interior passage. The interior passage, therefore, operationally connects the first and second ends of pipe and, thus, any other items that may be connected by, with or to on either end. The walls of pipe are configured and define the interior passage through which transmission may occur. In the current embodiment, pipe may be configured in any manner that promotes and allows for the transmission of the released 1-MCP gas from the generator to the control room. It is understood that the handling of 1-MCP gas is subject to various applicable rules, laws and regulations and, as such, the embodiments of the current invention promote and enable compliance with any such applicable rules, laws and regulations.

Operationally connected with the pipe is a one-way check valve and the air pump that provides a force, such as a blowing force. The blowing force may promote and provide for the establishment of a flow rate of the released 1-MCP gas during its transmission from the generator through pipe and to control room. In the current embodiment, the air pump is contemplated to provide a directional (blowing) force that promotes the released 1-MCP gas being transmitted from its initial location in the headspace of the mixing tank, into and through pipe and, ultimately, into control room. The blowing force provided by the air pump may vary, as shown throughout the instant application, to promote the efficient delivery of the released 1-MCP gas from the generator to control room. Further, in operational connection with pipe is a first flow meter that monitors the flow rate of the released 1-MCP. The current invention contemplates the presence of at least some amount of air that is present and mixed with the released 1-MCP gas. Therefore, it is understood that the released gas, transmission, flow and flow rate of the 1-MCP gas can comprise, to some extent, 1-MCP/air mixture.

In operation, system, via any process and method enabled by generator, as have been described herein, generates the release of 1-MCP gas. The released 1-MCP gas is initially located within a second area of the mixing tank. The second area is understood and typically referred to as a "headspace". The headspace allows for the released 1-MCP gas to remain separated from a mixture or mixture solution (as defined throughout) established within a first area. The first area is understood and typically referred to as a "receptacle" area or other commonly employed designators for indicating a location within which a mixture or mixture solution can be stored and contained.

The operational connection of pipe with the generator places the end of the pipe that is to be connected in a position proximal to the headspace of the mixing tank. It is understood that the devices, mechanisms and technologies employed to provide the operational connection of pipe with the generator may vary and include any connection capabilities contemplated by those skilled in the art. By this, it shall be understood, that the connection of pipe with generator shall provide an operational connection between the headspace and one of the open ends of pipe, thereby, providing for the connection of the interior passage of pipe with the generator. It is contemplated that this operational connection shall ensure that at least some portion of the open end of pipe connected with generator is at least partially exposed to the headspace of mixing tank. In preferred embodiments, the full opening providing by the open end of pipe that is connected with the generator is fully exposed to the headspace. It is contemplated that some portion of the open end of pipe may be at least partially submerged within the mixture contained in the mixing tank. Therefore, it is understood that the exact position of the connection of any of the mechanisms, devices and/or technologies employed for the transmission system with the generator may vary.

Positioned at least some distance from the first flow meter, typically at an opposite end of pipe, a second flow meter can be operationally connected with pipe to monitor the flow rate of the released 1-MCP (aka., 1-MCP/air mixture) prior to the gas entering the control room. A safety valve can also be operationally connected with pipe to avoid excessive pressure buildup within the system, particularly within pipe and generator. The positioning of the safety valve may vary as contemplated by those skilled in the art.

For any of the process, method and system embodiments of releasing 1-MCP gas described and shown for the current embodiment it is understood that it can further provide a desirable foam by-product profile by promoting the reduction and/or avoidance of foam by-product generation and can promote formation of a compliant impurity profile for the released 1-MCP gas in accordance with the current invention. Thus, the methods promote and can provide for greater than 96%, more preferably 100%, of 1-MCP gas being released from the carrier complex. The amount of carrier complex ranges from 0.001 kg to 10 kg, preferably 0.01 kg to 6 kg and more preferably 0.02 kg to 1 kg and the ratio of carrier complex to water ranges from 1:500 to 1:5 and more preferably 1:100 to 1:10. The carrier complex can be placed directly into the water in the interior space of the mixing tank or, at least initially, indirectly placed into contact with the water in the mixing tank by being contained in at least one of a water soluble and/or dissolvable polyvinyl alcohol pouch, water soluble and/or dissolvable paper bag and various other water soluble and/or dissolvable containers, films or pouches as may be contemplated. The carrier that can be complexed with 1-MCP to form the carrier complex can comprise one or more of an encapsulant(s) and/or adsorbent(s), preferably α-cyclodextrin, metal organic framework, zeolites, activated carbons, cucurbit[6]uril, and other polymeric or porous materials such as gelatin and pectin.

EXAMPLES

Example 1: Release of 1-MCP from α-Cyclodextrin Using Water with Different Physical Means Around 0.02 g of α-cyclodextrin/1-MCP powder was weighed and placed in a 250 mL glass jar equipped with a VICI valve for headspace sampling, and 20 mL of deionized water was injected into the glass jar through VICI valve. The valve was closed immediately after water injection. Three modes of rotation methods were used: (1) two dimensional rotation on a laboratory shaker under 50 rpm, (2) stirring using a magnetic stir bar under 50 rpm, and (3) three dimensional rotation on a laboratory shaker under 50 rpm, and a support was attached to the bottom center of the glass jar to create a tilt angle of 30°. A stagnant sample was used as control. Headspace was withdrawn periodically for GC/FID analysis. GC analysis followed CIPAC method 767, with operating conditions listed in Table 1.

TABLE 1

| GC condition for 1-MCP measurement | |
|---|---|
| GC type | Agilent 6890 Plus |
| Column | CP-PoraBOND Q, 25 m length, 0.25 mm i.d., 3 μm film thickness |
| Temperature | Injector port: 75° C. |
| | Detector: 200° C. |
| | Oven. 75° C. for 1 min, ramp 5° C./min, 110° C. (total 8 min) |
| Carrier gas | Helium |
| Flow rates (mL/min): | Helium: 30 |
| | Detectors |
| | Air: 400 |
| | Hydrogen: 45 |

Results (Table 2) show that 100% release of 1-MCP was achieved within 90 min under all three physical means, while only around 35% of 1-MCP was released from the stagnant sample (control) in the same period of time.

TABLE 2

Release of 1-MCP using three physical methods

| | % of release | | | |
|---|---|---|---|---|
| Time | 2 dimensional rotation | Stirring | 3 dimensional rotation | Stagnant (control) |
| 15 min | 20.5 | 35.8 | 26.8 | 5.2 |
| 30 min | 43.5 | 56.2 | 49.3 | 13.5 |
| 45 min | 64.9 | 78.5 | 71.5 | 18.8 |
| 60 min | 82.5 | 96.8 | 89.6 | 26.3 |
| 75 min | 89.8 | 100 | 98.2 | 31.1 |
| 90 min | 100 | 100 | 100 | 35.2 |

Example 2: Release of 1-MCP from α-Cyclodextrin Using Physical Means Versus Air Bubbling Generator Around 1 g α-cyclodextrin/1-MCP powder was packed in Polyvinyl alcohol pouch. Two pouches were prepared. One pouch was placed in a 3 dimensional rotation generator (100 rpm, 15° tilt angle) containing 100 mL deionized water. The other pouch was placed in an air bubbling generator consisting of 200 mL flat bottom glass beaker (containing 100 mL deionized water) and an air pump. An air dispenser was connected to the pump using a plastic tube and immersed under water. The two generation systems were placed into a 10 L glass chamber equipped with gas sampling port separately. Once the generator was turned on, the chamber was immediately sealed, and headspace sample was withdrawn for GC analysis. Same GC method as Example 1 was used.

Results (Table 3) show that complete release of 1-MCP was achieved using 3 dimensional rotation generator within 1 hour, while only around 58% was released using gas bubbling system in the same period of time. After extending the testing period for the gas bubbling system to 3 hours, only slight increase of 1-MCP in the headspace was observed. It was also observed that some portion of 1-MCP complex powder was pushed away by the air bubbles and deposited at the corner of the bottom of the glass beaker.

TABLE 3

1-MCP release using 3 dimensional rotation generator versus air bubbling generator

| | % of release | |
|---|---|---|
| Time | 3 dimensional rotation generator | Air bubbling generator |
| 15 min | 58.6 | 31.1 |
| 30 min | 88.5 | 49.5 |
| 60 min | 100 | 58.2 |
| 90 min | — | 61.5 |
| 120 min | — | 62.3 |
| 180 min | — | 63.5 |

Example 3: Impurity Profile of 1-MCP Released with and without Additive

This is example the potential effect of using other chemical additive on the purity of released 1-MCP. Around 0.02 g of α-cyclodextrin/1-MCP powder was weighed and placed in a 250 mL glass jar containing (1) 20 mL deionized water, and (2) 20 mL deionized water with 2% $CaCl_2$) (deliquescent agent listed in U.S. Pat. No. 6,426,319). Both jars were equipped with VICI valve for headspace measurement, and placed on a shaker under 100 rpm for 60 min. Headspace sample was withdrawn for GC analysis following CIPAC method 4667/m (Table 4).

TABLE 4

GC condition for 1-MCP impurity measurement

| GC type | Agilent 6890 Plus |
|---|---|
| Column | DB-624 30 m length × 0.25 mm i.d. × 1.4 μm film thickness |
| Injection system | Injector mode: spilt injection<br>Injector insert: 4 mm i.d., straight through glass (no glass wool)<br>Injection volume: 0.50 mL |
| Split flow | 20 mL/min |
| Detector | Flame ionization |
| Temperature | Injection port: 75° C.<br>Detector: 185° C.<br>Oven program: temp 1, 40° C., hold 0 min, ramp rate 25° C./min; temp 2, 165° C., hold 1 min |
| Gas flow rates | Helium (carrier): 2 mL/min; approximately 40 cm/sec<br>Air: 400 mL/min<br>Hydrogen: 45 mL/min<br>Nitrogen (make up): carrier flow + make up flow = 30 mL/min |

Results show (Table 5) that no 1-CMP or 3-CMP was detected using water alone, while 0.6% of 3-CMP in 1-MCP was found in 2% $CaCl_2$ solution, which failed to meet EPA standard of 0.05%.

TABLE 5

Impurity profile using different generation solution

| | 1-CMP | 3-CMP |
|---|---|---|
| Deionized water | Not detected | Not detected |
| Deionized water with 2% $CaCl_2$ | Not detected | 0.6% of 1-MCP |

Example 4: Foam Formation from Physical Rotation Versus Gas Bubbling

Around 6 g of α-cyclodextrin/1-MCP powder was packed in Polyvinyl alcohol pouch and placed in 200 mL glass beaker. Five generation methods were employed: (1) 2 dimensional rotation in 100 mL water under 200 rpm, (2) 2 dimensional rotation in 100 mL water under 200 rpm and 15° tilt angle, (3) 200 rpm stirring in 100 mL water, (4) air bubbling using one air pump in 100 mL water, and (5) air bubbling using two air pump in 100 mL water. Foam height for each treatment was measured periodically. Results (Table 6) show that no foam was observed in samples using rotation and stirring methods, while foam formed by using air pump. The foam may cause overflow of water containing α-cyclodextrin/1-MCP from the generator, which may result in residual chemicals on the ground, which leads to worker safety risks and difficulty in cleaning.

TABLE 6

Foam formation from physical rotation versus air bubbling

| | Foam height (cm) | | | | |
|---|---|---|---|---|---|
| Time | 2 dimensional rotation | 3 dimensional rotation | Stirring | 1 air pump | 2 air pump |
| 10 min | No foam | | | 2.5 | 3.1 |
| 20 min | | | | 2.3 | 2.5 |
| 30 min | | | | 2.1 | 2.4 |
| 40 min | | | | 2.0 | 2.4 |
| 50 min | | | | 2.0 | 2.4 |
| 60 min | | | | 2.0 | 2.4 |

Example 5: Release of 1-MCP from α-Cyclodextrin Using a Stirring Generator

Around 1 g of α-cyclodextrin/1-MCP powder was packed in Polyvinyl alcohol pouch and placed into a stirring generator (shown in FIG. 1). Ventilation system was set to operate after 5 min of turning on the stirrer in the generator. The generator was placed in a high density polyethylene tent equipped with a gas sampling port. Headspace analysis was conducted using the same method of Example 1. Results (Table 7) show that complete release of 1-MCP was achieved in 60 min, and no 1-MCP was detected before the ventilation started to operate. The delay in 1-MCP in the initial period of time can allow operator to exit the treatment room with no to minimal exposure to 1-MCP.

TABLE 7

1-MCP release profile using a stirring generator

| Time | % release |
|---|---|
| 5 min | Not detected |
| 15 min | 41.5 |
| 30 min | 72.6 |
| 45 min | 98.3 |
| 60 min | 100 |

Example 6: Release of 1-MCP from α-Cyclodextrin Using Steam

A steam 1-MCP generator shown as FIG. 4 was used. Around 0.1 g of 1-MCP/α-cyclodextrin complex was placed on a piece of Tyvek™ film as a thin layer in the generator. Around 8 mL of water was placed in water reservoir. The whole generator was closed using a lid with ventilation, and placed in a closed chamber equipped with gas sampling port. Headspace analysis was conducted using the same method of Example 1. Results (Table 8) show that complete release of 1-MCP was achieved within 30 min.

TABLE 8

1-MCP release profile using steam generator

| Time | % release |
|---|---|
| 10 min | 95 |
| 20 min | 100 |

The current invention provides significant benefits over the prior art and/or previous means used to release 1-MCP gas because it avoids the use of bubbling air through a mixture of water and 1-MCP/carrier complex, thereby enabling the current invention to avoid the excessive generation of a foam by-product which can be the cause of liquid mixture spilling on the ground. In conjunction with this the current invention promotes the release of the 1-MCP gas with an impurity profile that is in compliance with EPA regulatory standards. The exemplary embodiments of the apparatus, systems and methods of the instant invention can be used by various parties, such as food product suppliers/distributors, for promoting a safer and more complete release of 1-MCP gas from a complex with a carrier. By promoting a more complete release of 1-MCP in gas form, it is contemplated that current invention can promote the generation of a higher volume or more 1-MCP gas that can be used to treat food products and can promote prolonged shelf-life of a food product and promote quality preservation by more effectively withstanding the negative conditions experienced during storage and transportation throughout the life-cycle of a food product than what had been provided previously in the art.

The invention has been described with references to various preferred embodiments. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

Figure 17:
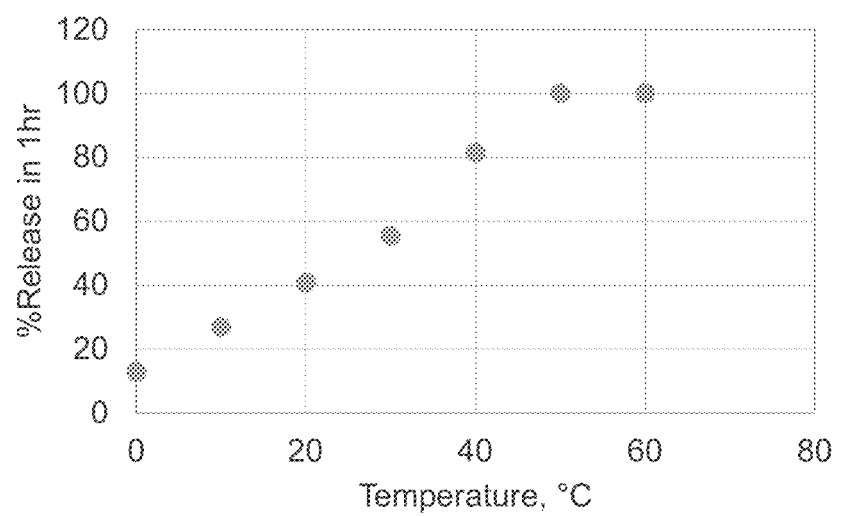
FIG. 17 is a plot diagram to demonstrate the effect of temperature on release of 1-MCP in 1 hour.

Example 7: Effect of Temperature of Mixing Solution on the Release of 1-MCP from α-Cyclodextrin Complex Around 11 g of α-cyclodextrin/1-MCP powder (2.5% 1-MCP) was weighed and placed in a stirring generator as described in FIG. 3 containing 1.3 L deionized water. Individual tests were conducted by varying water temperature between 0° C. and 60° C. A 120 rpm motor was used for the study. The generator was placed in an air tight chamber equipped with gas sampling port. The entire experimental setup was then placed at 0° C. Release percentage in the initial 1 hour was evaluated using the same method of Example 1. FIG. 17 and Table 9 demonstrate the effect of increasing temperature on the release of 1-MCP. Complete release was achieved within an hour when temperature was >50° C. and the clarity (indicator of dissolution of the encapsulation complex) of the solution is recorded in Table 9.

TABLE 9

Effect of temperature on release of 1-MCP and clarity of the solution in 1 hour

| Temperature (° C.) | % Release in 1 hr | Clarity of solution in 1 hour |
|---|---|---|
| 0 | 12.75 | Turbid |
| 10 | 26.86 | Turbid |
| 20 | 40.78 | Turbid |
| 30 | 55.41 | Turbid |
| 40 | 81.51 | Turbid |
| 50 | 100.00 | Clear in 0.75 hr |
| 60 | 100.00 | Clear in 0.5 hr |

Figure 18:
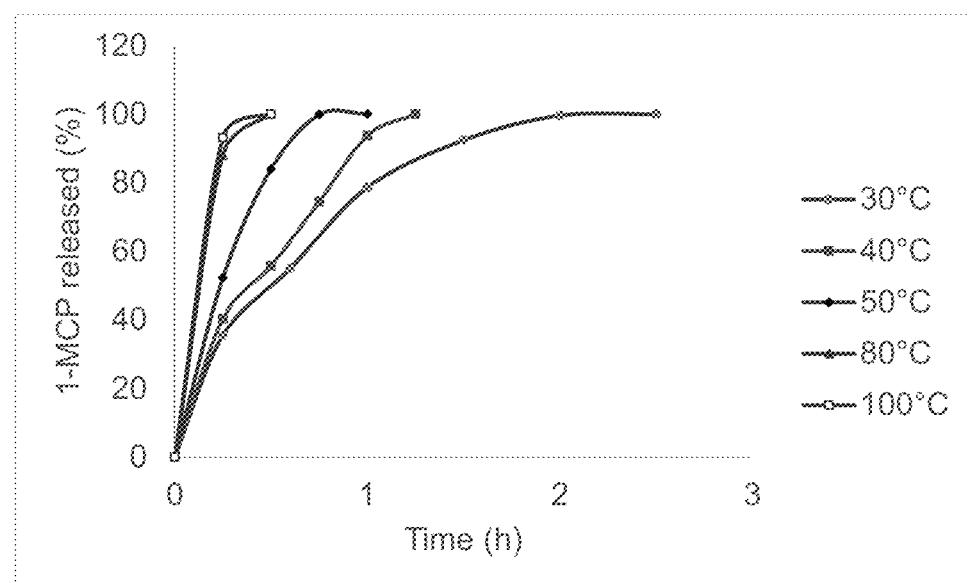
FIG. 18 is a plot diagram to demonstrate the effect of temperature and rpm on the release rate of 1-MCP.

Example 8: Effect of Temperature of Mixing Solution and Mixer Rpm on the Release Profile of 1-MCP from α-Cyclodextrin Complex Around 78 g of α-cyclodextrin/1-MCP powder (2.5% 1-MCP) was weighed and placed in a stirring generator as described in FIG. 3 containing 1.3 L deionized water. Individual tests were conducted by varying water temperature between 30° C. and 100° C. A 350 rpm motor was used for the study. The generator was placed in an air tight chamber equipped with gas sampling port. The entire experimental setup was then placed at 0° C. Release percentage over time was evaluated using the method as described in Example 1. FIG. 18 and Table 10 show that the high temperature combined with the relatively high mixing speed used in this example accelerated the release rate and shortened the time to achieve 100% release of 1-MCP.

TABLE 10

Effect of temperature and rpm on the release rate of 1-MCP

| 30° C. | | 40° C. | | 50° C. | | 80° C. | | 100° C. | |
|---|---|---|---|---|---|---|---|---|---|
| Time (h) | % Released | Time (h) | % Released | Time (h) | % Released | Time (h) | % Released | Time (h) | % Released |
| 0.00 | 0.00 | 0.00 | 0.00 | 0.00 | 0.00 | 0.00 | 0.00 | 0.00 | 0.00 |
| 0.25 | 35.42 | 0.25 | 40.27 | 0.25 | 52.20 | 0.25 | 88.12 | 0.25 | 93.11 |
| 0.60 | 55.02 | 0.50 | 55.72 | 0.50 | 83.92 | 0.50 | 100.00 | 0.50 | 100.00 |

TABLE 10-continued

Effect of temperature and rpm on the release rate of 1-MCP

| 30° C. | | 40° C. | | 50° C. | | 80° C. | | 100° C. | |
|---|---|---|---|---|---|---|---|---|---|
| Time (h) | % Released | Time (h) | % Released | Time (h) | % Released | Time (h) | % Released | Time (h) | % Released |
| 1.00 | 78.60 | 0.75 | 74.49 | 0.75 | 99.87 | | | | |
| 1.50 | 92.40 | 1.00 | 93.69 | 1.00 | 100.00 | | | | |
| 2.00 | 99.59 | 1.25 | 100.00 | | | | | | |
| 2.50 | 100.00 | | | | | | | | |

Throughout a 1-MCP release process the temperature control system of the current invention can promote and/or provide the establishment and maintenance of the mixture at a temperature range of 1° C. to 100° C. for at least 0.5 hours in the mixing tank. As shown throughout the instant application, it is contemplated that a temperature control system can promote and/or provide the establishment and maintenance of the mixture at a temperature range of 0° C. to 100° C. for various periods of time during a 1-MCP release process provided by the current invention. It is contemplated that the temperature control system of the current invention can also promote and/or provide the establishment and maintenance of a mixture at a temperature range as described both prior to and post the 1-MCP release process for various periods of time.

Example 9: Calculation of Cooling Constant of Generator Using New Law of Cooling The stirring generator as described in relation to FIG. 3, further including a temperature control system as described in relation to FIGS. 12-16, was filled with 12 L water and stirred with a motor at 220 rpm. A temperature logger was used to monitor the water (mixing solution) temperature every 15 min for 24 hours. Newton's law of cooling was used to calculate the cooling constant per hour, k based on the following equation, where T(t) is the temperature at time t, $T_s$ is the ambient temperature, and $T_0$ is the initial temperature.

$$T(t) = T_s + (T_0 - T_s)e^{-kt}$$

TABLE 11

Calculation of cooling constant per hour, k from cooling rate of water in 1-MCP generator

| Condition | Ambient Temp. ($T_s$), ° C. | Initial Temp. of Water ($T_0$), ° C. | Temp. at 15 hours T(t), ° C. | Cooling constant/ hr (k) |
|---|---|---|---|---|
| No insulation | 5.95 | 26 | 7.10 | 0.1906 |

This method as explained above can be used to calculate cooling constant (k) of the generator covered by insulating materials such as metalized bubble wrap, poly-fil insulation bag, etc. The experimental k value per hour for generator with metalized bubble wrap was 0.071 and for generator with Poly-fil insulation bag was 0.052. Generally speaking the lower the value of k, the better the insulation capability of the insulating material. For optimal 1-MCP release from the 1-MCP-encapsulant and/or adsorbent complex, the k value of the generator with or without insulation material is between 0.0000 to 0.1800, preferably 0.0001 to 0.1800 and more preferably, 0.001 to 0.1800. Persons with ordinary skills and art may employ a combination of higher initial solution temperature and a 1-MCP generator with higher k value per hour than as identified above (higher than 0.18) to achieve a similar 1-MCP release result as disclosed in the invention. For instance, if the starting temperature of the solution is 100° C., the temperature of the solution inside the 1-MCP generator with k value per hour of 2 will have resultant solution temperature pf 14.4° C. in 1 hour. Likewise, k value per hour of 1, will yield a resultant solution temperature of 37.4° C. in one hour; k value per hour of 0.5, will yield a resultant solution temperature of 61.0° C. in one hour; k value per hour of 0.2, will yield a resultant solution temperature of 82.0° C. in one hour; k value per hour of 0.1, will yield a resultant solution temperature of 90.5° C. in one hour; k value per hour of 0.05, will yield a resultant solution temperature of 95.2° C. in one hour; and k value per hour of 0.0, will yield a resultant solution temperature of 100.0° C. Therefore, with ordinary skill and art can achieve the temperature of the water (mixing solution) for at least portion of the 1-MCP Release Process, preferably in the range of 1-100° C., more preferably in the range of 10-80° C., most preferably in the range of 10-60° C.

Example 10: Effect of Insulation Material on Water Temperature Reduction

The stirring generator as described in FIG. 3 was filled with 12 L water and stirred with a motor at 220 rpm. A temperature logger was used to monitor the water (mixing solution) temperature every 15 min for 24 hours. The experiment was repeated by insulating the generator with insulation materials to slow down the rate of cooling of the water in the generator. The table below shows that based on the calculated cooling constant/hr, k from experiment, the predicted time for water of 25° C. to reduce to 12.5° C. in the insulated generator would be much longer than without insulation and different insulation materials and thickness would also result in different insulation effectiveness on maintaining water temperature.

TABLE 12

Water temperature profiles in the generators with different insulation materials

| Conditions | k | Predicted time (h) for water of 25° C. to reduce to 12.5° C., when ambient is 0° C. |
|---|---|---|
| No insulation | 0.191 | 3.64 |
| Metalized bubble wrap | 0.071 | 9.81 |
| Poly-fil insulation bag | 0.052 | 13.34 |

Another method of achieving the disclosed k values of the invention device between 0.00001 to 0.1800, may be obtained by increasing the thickness of the 1-MCP generating device. It is contemplated that the thickness of the 1-MCP generating device may refer to the dimensional configuration and construct provided, either individually or in any combination, to the mixing tank, insulation system components and such other features that may be included in establishing the device. Generally speaking, higher the thickness of the 1-MCP generating device, lower will be the k value of the device. Persons with ordinary skills and art may employ other methods to arrive at a similar or substantially similar k value of the 1-MCP generating device as disclosed in this invention.

Figure 19A:
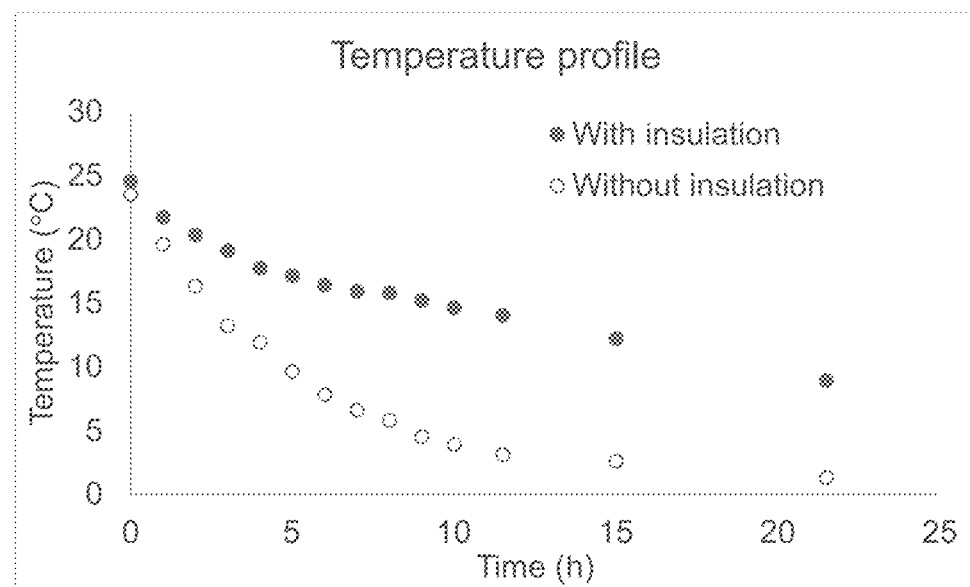
FIG. 19A is a plot diagram of the temperature using generator with and without insulation.
Figure 19B:
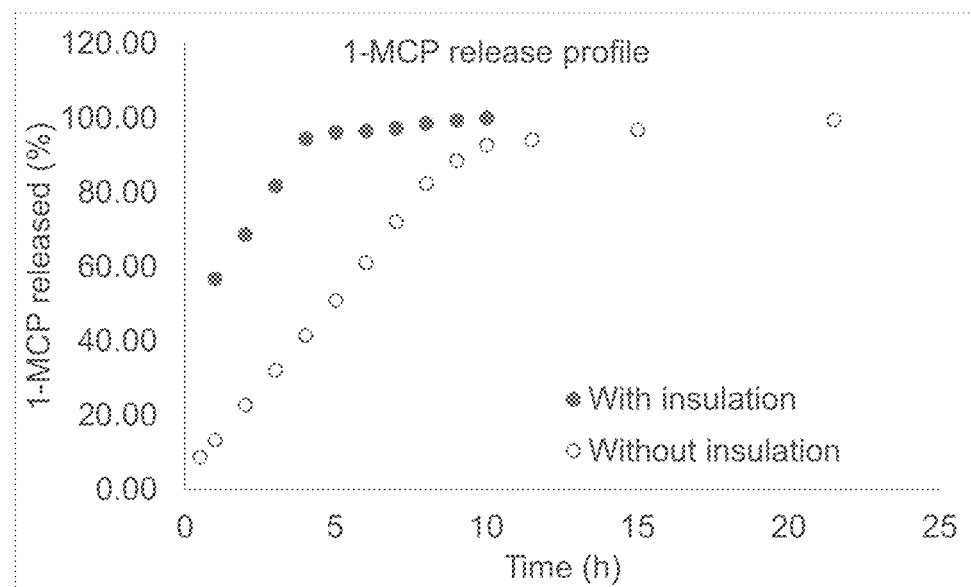
FIG. 19B is a plot diagram of the 1-MCP release profile using generator with and without insulation.

Example 11: Release of 1-MCP from α-Cyclodextrin Using a Generator with Temperature Insulation Around 100 g of α-cyclodextrin/1-MCP powder (2.5% 1-MCP) was weighed and placed in a stirring generator as described in FIG. 11 containing 12 L 25° C. deionized water. A 120 rpm motor was used for the study. An insulation wrap made of poly-fil was installed around the outside of the generator. The generator was placed in a refrigerated storage room with ambient temperature of 0-5° C. A generator without insulation containing 12 L 25° C. of water with 100 g of α-cyclodextrin/1-MCP powder was used as control. Gas sampling pumps connected with sampling bags were programmed to withdraw samples periodically. Sample analysis of the gas collected was conducted using the method of Example 1. Temperature of the releasing solution was monitored using a temperature logger. FIG. 19 and Table 13 show that the generator with insulation had slower temperature reduction in releasing solution and faster release rate of 1-MCP than without insulation. Complete release was achieved within 10 hours in the insulated generator, while the release from the non-insulated generator was complete in 21.5 hours.

TABLE 13

Temperature and 1-MCP release % using generator with and without insulation

| Time (hour) | Generator with insulation | | Generator without insulation | |
|---|---|---|---|---|
| | Solution temperature (° C.) | % released | Solution temperature (° C.) | % released |
| 0 | 24.5 | 0.0 | 24.0 | 0.0 |
| 1 | 21.7 | 56.6 | 19.6 | 13.3 |
| 2 | 20.3 | 68.6 | 16.3 | 22.7 |
| 3 | 19.1 | 81.7 | 13.2 | 32.1 |
| 4 | 17.7 | 94.4 | 11.9 | 41.4 |
| 5 | 17.1 | 96.0 | 9.6 | 50.8 |
| 6 | 16.4 | 96.5 | 7.8 | 61.0 |
| 7 | 15.9 | 97.2 | 6.6 | 72.1 |
| 8 | 15.8 | 98.5 | 5.8 | 82.3 |
| 9 | 15.2 | 99.3 | 4.5 | 88.5 |
| 10 | 14.6 | 100.0 | 3.9 | 92.7 |
| 11.5 | 14 | 100.0 | 3.1 | 94.1 |
| 15 | 12.2 | 100.0 | 2.6 | 96.8 |
| 21.5 | 8.9 | 100.0 | 1.3 | 100.0 |

Figure 20:
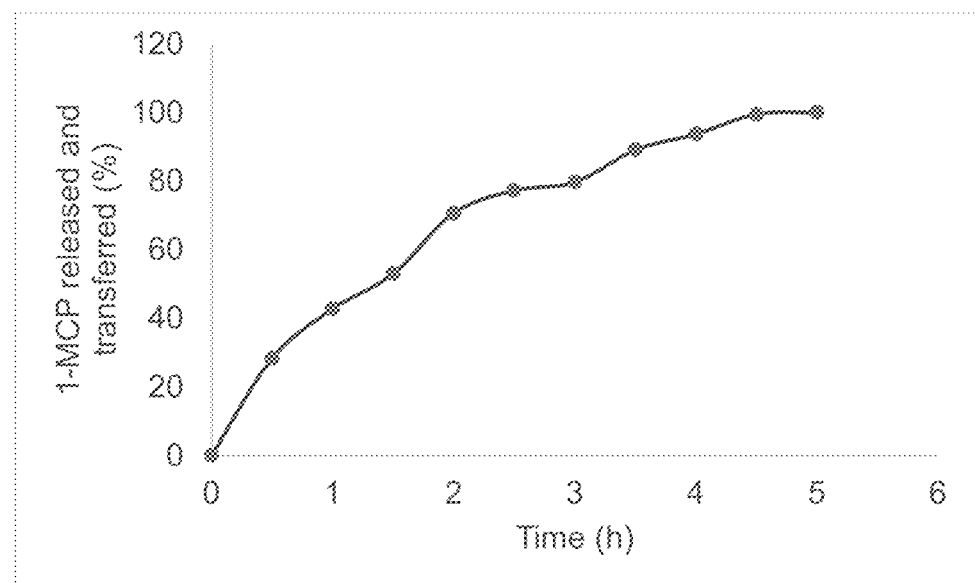
FIG. 20 is a plot diagram of the percentage of 1-MCP released from complex and transferred to the simulated storage room over time using set-up shown in FIG. 13.

Example 12: Release of 1-MCP from α-Cyclodextrin Using a Generator Placed Outside of a Storage Room, where the Air is Flushed in the Headspace of the Generator Around 3.5 g of α-cyclodextrin/1-MCP powder (2.5%) was weighed and placed in a stirring generator (total volume of 475 mL) similar to the system described in FIG. 13. The generator contained 285 mL deionized water (25° C.). An air pump (0.1 L/min) was equipped on the generator to connect to a 495 L closed chamber as a simulated storage room. Depending on the size of the application room, the capacity of the air pump may vary. The larger the size of the application room, the larger would be the capacity of the air pump. Gas samples from the chamber were withdrawn for GC/FID analysis using the same method of Example 1. FIG. 20 and Table 14 show that complete release of 1-MCP was achieved in 5 hours and all the released 1-MCP was transferred from the generator to the chamber.

TABLE 14

Percentage of 1-MCP released from complex and transferred to the simulated storage room over time using set-up shown in FIG. 13

| Time (h) | % Released and transferred |
|---|---|
| 0.00 | 0.00 |
| 0.50 | 28.29 |
| 1.00 | 42.71 |
| 1.50 | 53.00 |
| 2.00 | 70.58 |
| 2.50 | 77.27 |
| 3.00 | 79.67 |
| 3.50 | 89.10 |
| 4.00 | 93.68 |
| 4.50 | 99.50 |
| 5.00 | 100.00 |

Figure 21:
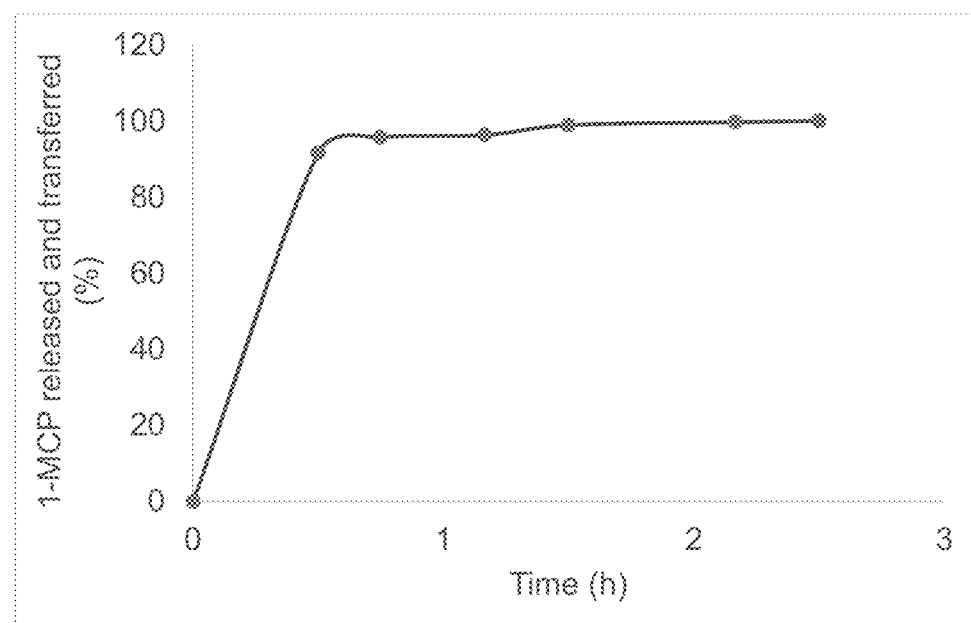
FIG. 21 is a plot diagram of the percentage of 1-MCP released from complex and transferred to the simulated storage room over time using set-up shown in FIG. 14.

Example 13: Release of 1-MCP from α-Cyclodextrin Using a Generator Placed Outside of a Storage Room, where Air is Flushed into the Mixing Solution Around 3.5 g of α-cyclodextrin/1-MCP powder (2.5%) was weighed and placed in a stirring generator (total volume of 475 mL) similar to the system described in FIG. 14. The generator contained 285 mL deionized water (25° C.). An air pump (0.1 L/min) was equipped on the generator to connect to a 495 L closed chamber as a simulated storage room. Gas samples from the chamber were withdrawn for GC/FID analysis using the same method of Example 1. FIG. 21 and Table 15 show that complete release of 1-MCP was achieved in 2.5 hours and all the released 1-MCP was transferred from the generator to the chamber.

TABLE 15

Percentage of 1-MCP released from complex and transferred to the simulated storage room over time using set-up shown in FIG. 14

| Time (h) | % Released and transferred |
|---|---|
| 0.00 | 0.00 |
| 0.50 | 91.51 |
| 0.75 | 95.70 |
| 1.17 | 96.35 |
| 1.50 | 98.92 |
| 2.17 | 99.76 |
| 2.50 | 100.00 |

Figure 22:
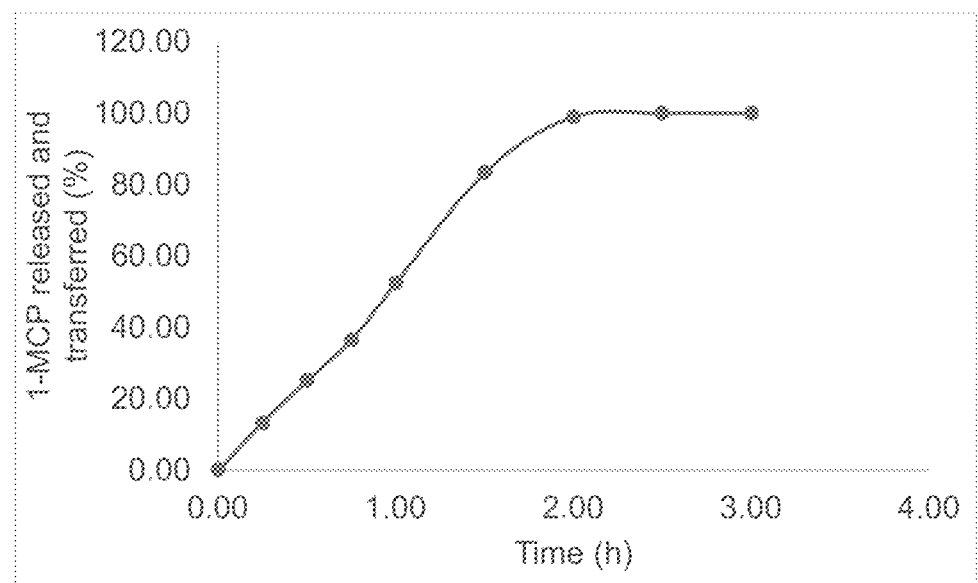
FIG. 22 is a plot diagram of the percentage of 1-MCP released from complex in simulated storage room over time using set-up shown in FIG. 14 with 50° C. warm water.

Example 14: Release of 1-MCP from α-Cyclodextrin Using an Insulated Generator with Warm Water Placed Outside of a Storage Room, where Air is Flushed into the Mixing Solution Around 17.1 g of α-cyclodextrin/1-MCP powder (2.5%) was weighed and placed in a stirring generator (total volume of 475 mL) similar to the system described in FIG. 14. The generator contained 285 mL deionized water (50° C.). An air pump (0.1 L/min) was equipped on the generator to connect to a 495 L closed chamber as a simulated storage room. Gas samples from the chamber were withdrawn for GC/FID analysis using the same method of Example 1. FIG. 22 and Table 16 show that complete release of 1-MCP was achieved in 3 hours and all the released 1-MCP was transferred from the generator to the chamber.

TABLE 16

Percentage of 1-MCP released from complex in simulated storage room over time using set-up shown in FIG. 14 with 50° C. warm water

| Time (h) | % Released and transferred |
|---|---|
| 0.00 | 0.00 |
| 0.25 | 13.24 |
| 0.50 | 25.13 |
| 0.75 | 36.46 |
| 1.00 | 52.46 |
| 1.50 | 83.45 |
| 2.00 | 99.05 |
| 2.50 | 100.00 |
| 3.00 | 100.00 |

Figure 23:
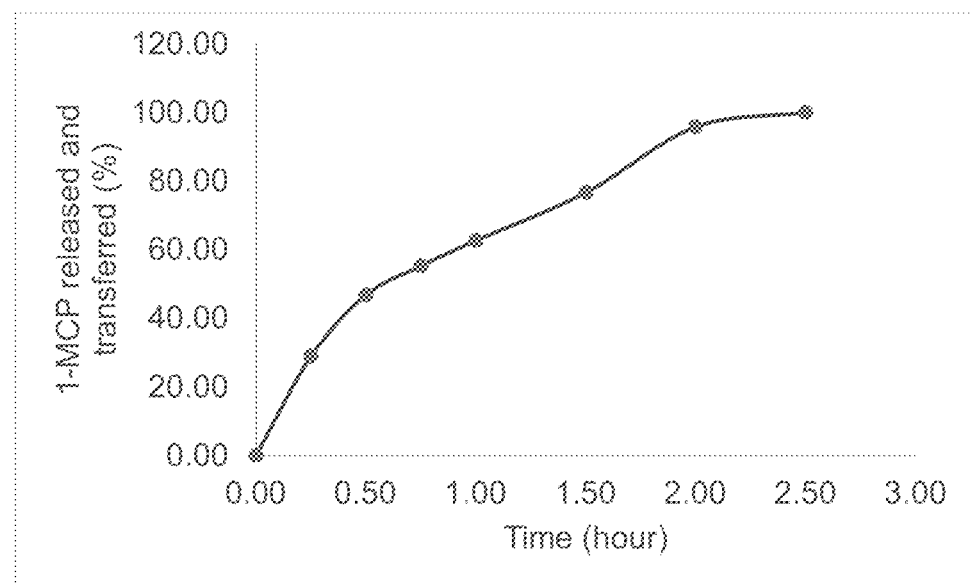
FIG. 23 is a plot diagram of the percentage of 1-MCP released from complex and transferred to the simulated storage room over time using set-up shown in FIG. 15.

Example 15: Release of 1-MCP from α-Cyclodextrin Using a Generator Placed Outside of a Storage Room, where the Generated 1-MCP was Withdrawn from the Generator and Pumped into the Storage Room Using a Vacuum Pump Around 3.5 g of α-cyclodextrin/1-MCP powder (2.5%) was weighed and placed in a stirring generator (total volume of 475 mL) similar to the system described in FIG. 15. The generator contained 285 mL deionized water (25° C.). An air pump (0.1 L/min) was equipped on the generator to connect to a 495 L closed chamber as a simulated storage room. Gas samples from the chamber were withdrawn for GC/FID analysis using the same method of Example 1. FIG. 23 and Table 17 show that complete release of 1-MCP was achieved in 2.5 hours and all the released 1-MCP was transferred from the generator to the chamber.

TABLE 17

Percentage of 1-MCP released from complex and transferred to the simulated storage room over time using set-up shown in FIG. 15

| Time (h) | % Released and transferred |
|---|---|
| 0.00 | 0.00 |
| 0.25 | 28.90 |
| 0.50 | 46.75 |
| 0.75 | 55.26 |
| 1.00 | 62.64 |
| 1.50 | 76.66 |
| 2.00 | 95.80 |
| 2.50 | 100.00 |

Figure 24:
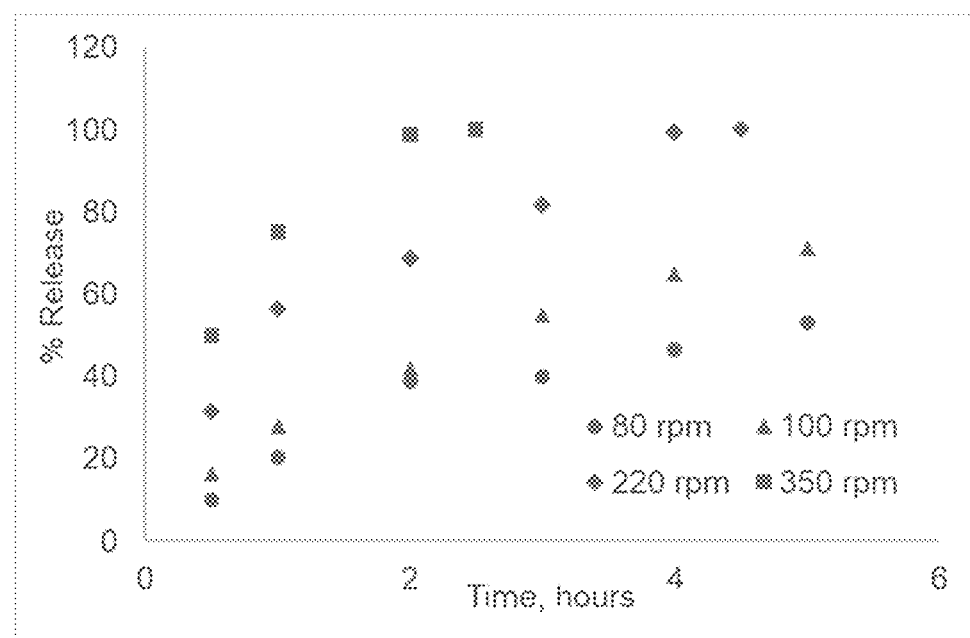
FIG. 24 is a plot diagram showing the effect of rpm on 1-MCP release rate from complex.
Figure 25:
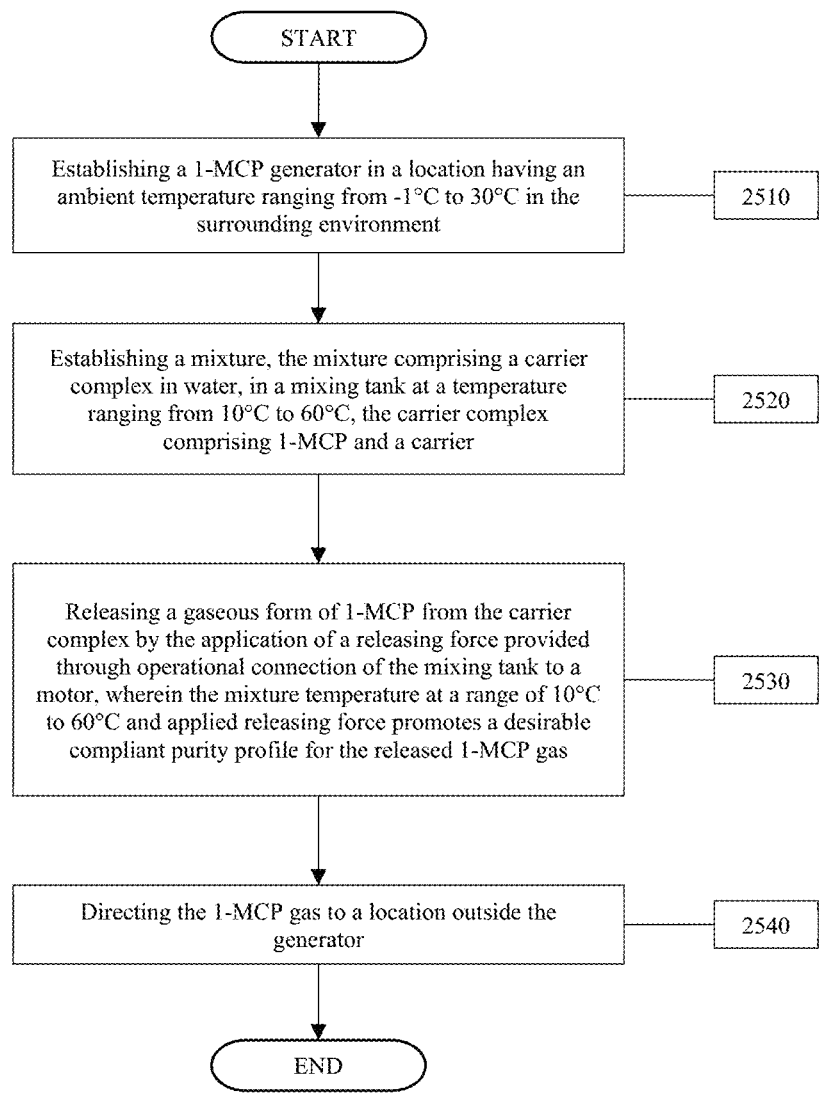
FIG. 25 is a block diagram showing a seventh preferred method for releasing a 1-MCP gas in accordance with an exemplary embodiment of the current invention.

Example 16. Release of 1-MCP from α-Cyclodextrin Using Differing Rpm from a Generator Around 11 g of α-cyclodextrin/1-MCP powder (2.5% 1-MCP) was weighed and placed in a stirring generator as described in FIG. 3 containing 1.3 L deionized water. The water temperature in the generator was set at 22-25° C. and the test was conducted under 0° C. Individual tests were conducted by varying the rpm of the mixing rod or stirrer. The generator was placed in an air tight chamber equipped with gas sampling port and the chamber was then placed at 0° C. The percentage release of 1-MCP from the complex was evaluated over 5-hour period using the same method of Example 1. FIG. 24 and Table 18 demonstrates the effect of rpm on the rate of release, wherein the increasing rpm increases the rate of release.

TABLE 18

Effect of rpm on 1-MCP release rate

| 80 rpm | | 100 rpm | | 220 rpm | | 350 rpm | |
|---|---|---|---|---|---|---|---|
| Time (h) | Release % | Time (h) | Release % | Time (h) | Release % | Time (h) | Release % |
| 0.5 | 10.03 | 0.5 | 16.25 | 0.5 | 31.52 | 0.5 | 50.02 |
| 1 | 20.39 | 1 | 27.96 | 1 | 56.62 | 1 | 75.2 |
| 2 | 38.59 | 2 | 41.98 | 2 | 68.64 | 2 | 98.7 |
| 3 | 39.86 | 3 | 54.95 | 3 | 81.72 | 2.5 | 100 |
| 4 | 46.57 | 4 | 64.77 | 4 | 99.38 | | |
| 5 | 53.14 | 5 | 71.26 | 4.5 | 100.00 | | |

The current invention provides significant benefits over the prior art and/or previous generator and 1-MCP releasing technologies. The exemplary embodiments of the generator, methods for releasing 1-MCP gas and systems for providing the methods for releasing 1-MCP gas of the instant invention can be used by various food product suppliers/distributors for promoting the efficient application of the methods for releasing 1-MCP gas and, to the extent involved, the extension of the shelf life of food products. Use of the current invention promotes and also allows for an efficient application of released 1-MCP gas to food products in units of varying amounts (single to multiple items), volumes, weights and sizes further supporting marketing applications that may be geared towards more non-traditional outlets, such as the convenience store market. Still further, the release and application of the 1-MCP gas to food products as provided in embodiments of the current invention promote quality preservation by more effectively withstanding the negative conditions experienced during transportation throughout the distribution and handling from the country or countries of production to the consuming markets than what had been provided previously in the art. The improved capabilities provided by the current invention promote and allow for a more efficient and effective release and application of 1-MCP gas and further help to promote safer work environments for humans. The current invention can promote various additional commercially advantageous characteristics, such as further promoting improved production capabilities, reducing wastage, and/or improving workplace safety and satisfaction.

The invention has been described with references to various preferred embodiments. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A method of releasing 1-MCP gas comprising:
   establishing a mixture of water and a carrier complex, the carrier complex comprising 1-MCP complexed with at least one carrier, the carrier consisting of at least one of an encapsulant(s) and adsorbent(s), in an interior space of a removable mixing tank;
      wherein the mixture is maintained at a temperature range of 1° C. to 100° C. for at least 0.5 hours in the removable mixing tank by a temperature control system,
   releasing 1-MCP gas from the carrier complex by the application of a releasing force consisting of at least one of a rotational, stirring, spinning, vibrational, shaking, oscillatory, gyratory and steam force, the releasing force provided through operational connection of the removable mixing tank to a force generation mechanism, wherein the applied releasing force promotes 1-MCP dissociation from the carrier and release of 1-MCP gas, the released 1-MCP gas having a compliant impurity profile and a desirable foam by-product profile;
      wherein the compliant impurity profile is at least one of below 0.1% of the total 1-MCP gas released and the levels of chlorinated compounds 1-chloro-2-methylpropene (1-CMP) and 3-chloro-2-methylpropene (3-CMP) below 0.05% of total 1-MCP gas released; and
   wherein the desirable foam by-product profile comprises air trapped in hydrophilic and hydrophobic groups on alpha-cyclodextrin in amounts that avoid spillage from the removable mixing tank.

2. The method of claim 1, wherein 1-MCP gas release process occurs within a 1-MCP generator comprising the removable mixing tank operationally connected with the force generation mechanism and application of the released 1-MCP gas to respiring produce is conducted through operational connection of the 1-MCP generator to a secondary location.

3. The method of claim 2, wherein the released 1-MCP is delivered and applied to respiring produce within the secondary location through a pipe with a diameter ranging from 0.001 to 2 meters.

4. The method of claim 2, wherein the released 1-MCP gas is delivered to the secondary location by creating a pressure difference between the 1-MCP generator and the secondary location using a gas pumping mechanism consisting of at least one of the equipment of air compressors, portable gas tanks, and air pumps at gas flow rate between 0.001 to 200 L/min.

5. The method of claim 2, wherein the release of 1-MCP gas occurs within a headspace of the 1-MCP generator located outside of a storage room, released 1-MCP gas is transferred from the headspace to the storage room using at least one of an air pump and vacuum pump.

6. The method claim 2, wherein the secondary location provides a controlled atmosphere storage comprising at least one of 0.1 to 5% O2 and 0.0 to 3% CO2.

7. The method of claim 1, wherein a cooling constant ranges from 0.00001 to 0.1800 per hour.

8. The method of claim 1, wherein greater than ninety-six percent (>96%) of 1-MCP gas is released from the carrier complex.

9. The method of claim 1, wherein the carrier complex ranges from 0.001 kg to 10 kg and the ratio of carrier complex to water ranges from 1:500 to 1:5.

10. The method of claim 1, wherein the temperature control system comprises one or more insulation material consisting of at least one of (i) fiberglass, (ii) mineral wool, (iii) cellulose, (iv) natural fibers, (v) polystyrene, (vi) polyisocyanurate, (vii) polyurethane, (viii) vermiculite, (ix) perlite, (x) urea-formaldehyde foam, (xi) cementitious foam, (xii) phenolic foam and (xiii) air, and wherein the one or more insulation material (i) covers 5% to 100% of at least one of the removable mixing tank and force generation mechanism; and (ii) has a thickness, except for air, ranging from 0.001 to 1 meter.

11. The method of claim 1, wherein the force generation mechanism comprises at least one of a motor and generator and is operationally connected with a mixing mechanism to promote the application of the releasing force.

12. A method of releasing 1-MCP gas comprising:
   establishing a mixture of water and a carrier complex, the carrier complex comprising 1-MCP complexed with at least one carrier, the carrier consisting of at least one of an encapsulant(s) and adsorbent(s), that comprises at least one of a α-cyclodextrin, metal organic framework, zeolites, activated carbons, cucurbit[6]uril, and other polymeric and porous materials in an interior space of a removable mixing tank;
      wherein the mixture is maintained in a temperature range of 1° C. to 100° C. for at least 0.5 hours;
   releasing 1-MCP gas from the carrier complex by the application of a releasing force consisting of at least one of a rotational, stirring, spinning, vibrational, shaking, mixing, oscillatory, gyratory and steam, the releasing force provided through operational connection of the removable mixing tank to a force generation mechanism, wherein the applied releasing force promotes 1-MCP dissociation from the carrier and release of 1-MCP gas, the released 1-MCP gas having a compliant impurity profile; and
   wherein the compliant impurity profile is at least one of below 0.1% of the 1-MCP gas released and levels of chlorinated compounds 1-chloro-2-methylpropene (1-CMP) and 3-chloro-2-methylpropene (3-CMP) below 0.05% of 1-MCP gas released.

13. The method of claim 12, wherein 1-MCP gas release process occurs within a 1-MCP generator comprising the removable mixing tank operationally connected with the force generation mechanism and application of the released 1-MCP gas to respiring produce is conducted through operational connection of the 1-MCP generator to a secondary location, wherein the secondary location provides a controlled atmosphere storage comprising at least one of 0.1 to 5% O2 and 0.0 to 3% CO2.

14. The method of claim 13, wherein the released 1-MCP is delivered and applied to respiring produce within the secondary location through a pipe with a diameter ranging from 0.001 to 2 meters.

15. The method of claim 14, wherein the released 1-MCP gas is delivered to the secondary location by creating a pressure difference between the 1-MCP generator and the secondary location using a gas pumping mechanism consisting of at least one of the equipment of air compressors, portable gas tanks, and air pumps at gas flow rate between 0.001 to 200 L/min.

16. The method of claim 13, wherein the release of 1-MCP gas occurs within a headspace of the 1-MCP generator located outside of a storage room and released 1-MCP gas is transferred from the headspace to the storage room using at least one of a vacuum pump and air pump.

17. The method of claim 12, wherein greater than ninety-six percent (>96%) of 1-MCP gas is released from the carrier complex and the carrier complex ranges from 0.02 kg to 6 kg and the ratio of carrier complex to water ranges from 1:500 to 1:5.

18. The method of claim 12, wherein the application of the releasing force is in at least one or more of (i) a continuous manner and (ii) intermittent manner and in at least one of two and three dimensions and further comprises the application of at least two releasing forces in at least one of (i) isolation from; (ii) sequentially to and (iii) concurrently with one another.

19. The method of claim 12, wherein the carrier complex is at least one of placed directly into the water in the interior space of the removable mixing tank and contained in at least one of a water permeable materials, water soluble materials, water soluble paper bag and water soluble pouch.

20. The method of claim 12, wherein the force generation mechanism comprises at least one of a motor and generator and is operationally connected with a mixing mechanism to promote the application of the releasing force.

\* \* \* \* \*